United States Patent [19]

Maienfisch

[11] Patent Number: 4,871,719

[45] Date of Patent: Oct. 3, 1989

[54] COMPOSITION FOR CONTROLLING PARASITES IN PRODUCTIVE LIVESTOCK

[75] Inventor: Peter Maienfisch, Aesch, Switzerland

[73] Assignee: Ciba-Geigy Corporation, Ardsley, N.Y.

[21] Appl. No.: 168,766

[22] Filed: Mar. 16, 1988

[30] Foreign Application Priority Data

Mar. 24, 1987 [CH] Switzerland .......................... 1117/87
Dec. 15, 1987 [CH] Switzerland .......................... 4878/87

[51] Int. Cl.⁴ .................... A61K 31/35; A61K 31/695; C07D 493/22; C07D 313/06
[52] U.S. Cl. ...................................... 514/63; 549/214; 549/268; 549/265; 549/4; 549/60; 549/88; 546/14; 546/15; 544/70; 544/229; 544/230; 544/6; 544/69; 548/110; 548/127; 548/129; 548/128; 548/131; 548/132; 548/134; 548/135; 548/136; 548/142; 548/143; 548/147; 548/216; 548/206; 548/243; 548/247; 548/251; 548/253; 548/348; 548/374; 548/256; 548/265; 548/336; 548/406; 548/407; 548/950; 548/952; 514/228.5; 514/232.8; 514/256; 514/252; 514/253; 514/321; 514/328; 514/374; 514/376; 514/378; 514/380; 514/382; 514/383; 514/384; 514/406; 514/407; 514/409; 514/369; 514/365; 514/372; 514/361; 514/362; 514/363; 514/369; 514/210; 514/430; 514/444; 514/450
[58] Field of Search ..................... 549/264, 4, 265, 60, 549/214, 88; 514/450, 63, 228.5, 232.8, 256, 252, 253, 321, 338, 374, 376, 378, 380, 382, 383, 384, 406, 407, 369, 365, 372, 397, 409, 361, 362, 363, 364, 210, 430, 444; 546/14, 15; 544/70, 229, 230, 6, 69; 548/110, 127, 128, 129, 131, 132, 134, 135, 136, 142, 143, 147, 216, 206, 243, 247, 214, 348, 374, 251, 253, 256, 262, 265, 336, 406, 407, 950, 952

[56] References Cited

U.S. PATENT DOCUMENTS 3,950,360  4/1976  Aoki et al. ................... 260/343.2 R
4,173,571 11/1979  Chabala et al. ............... 260/343.41
4,328,335  5/1982  Mrozik ........................ 536/7.1
4,346,171  8/1982  Takiguchi et al. ............. 435/119
4,778,809 10/1988  Maienfisch ................... 514/450

FOREIGN PATENT DOCUMENTS 2166436 5/1986 United Kingdom .

Primary Examiner—Richard L. Raymond
Assistant Examiner—Mark W. Russell
Attorney, Agent, or Firm—Edward McC. Roberts

[57] ABSTRACT

Novel 13-spiro-2'-[tetrahydrofuran]-milbemycins of the formula I

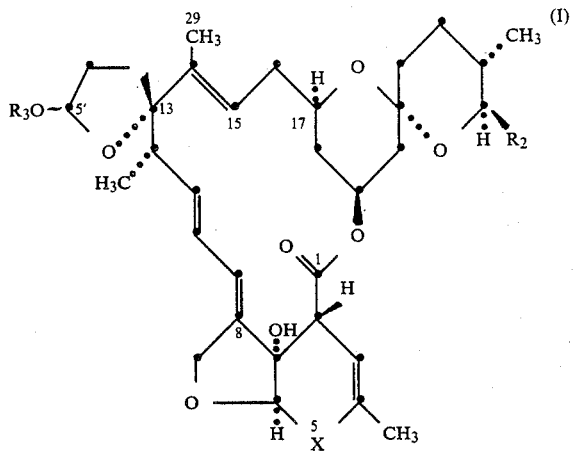

in which

X represents one of the groups —CH(OR$_1$)—, —C(=O)— or —C(=N—OH)—;

R$_1$ represents hydrogen or a OH-protecting group;

R$_2$ represents methyl, ethyl, isopropyl or sec.-butyl or the group —C(CH$_3$)=CH—A in which A represents methyl, ethyl or isopropyl; and R$_3$ represents hydrogen; C$_1$–C$_{10}$-alkyl; C$_1$–C$_{10}$-alkyl substituted by at least one substituent selected from the group consisting of halogen, C$_1$–C$_6$-alkoxy, C$_2$–C$_6$-alkoxyalkoxy, C$_3$–C$_9$-alkoxyalkoxyalkoxy, C$_1$–C$_6$-alkylthio, C$_3$–C$_7$-cycloalkyl, C$_1$–C$_3$-alkyl-substituted C$_3$–C$_7$-cycloalkyl, hydroxy, benzyloxy, C$_1$–C$_6$-acyl and C$_1$–C$_6$-acyloxy, it being possible for each of the above-mentioned radicals representing or containing an alkoxy group to be terminally substituted at a terminal alkoxy group by hydroxy, halogen, C$_1$–C$_6$-acyl or by C$_1$–C$_6$-acyloxy; C$_3$–C$_7$-cycloalkyl; C$_3$–C$_7$-cycloalkyl substituted by at least one substituent selected from the group consisting of halogen and C$_1$–C$_3$-alkyl; C$_3$–C$_7$-cycloalkenyl; C$_2$–C$_{10}$-alkenyl; C$_2$–C$_{10}$-alkynyl; a radical selected from the group consisting of C$_2$–C$_{10}$-alkenyl and C$_2$–C$_{10}$-alkynyl, which radical is substituted by halogen, C$_1$–C$_6$-alkoxy or by C$_1$–C$_6$-acyloxy; 1-adamantylmethyl; menthyl; carveyl; phenyl; benzyl; napthyl; a radical selected from the group consisting of phenyl, benzyl and naphthyl, which radical is substituted by at least one substituent selected from the group consisting of halogen, C$_1$–C$_3$-alkyl, C$_1$–C$_3$-haloalkyl, C$_1$–C$_3$-alkoxy, C$_1$–C$_3$-haloalkoxy, C$_1$–C$_3$-alkylthio, nitro and cyano; benzyl substituted by a phenoxy group; or a four- to six-membered heterocyclic radical that has from one to three hetero atoms selected from the group consisting of oxygen, sulphur and nitrogen and that is unsubstituted or is substituted by at least one substituent selected from the group consisting of halogen, C$_1$–C$_3$-alkyl, C$_1$–C$_3$-haloalkyl, C$_1$–C$_3$-alkoxy, C$_1$–C$_3$-haloalkoxy, C$_1$–C$_3$-alkylthio, nitro and cyano, it being possible for the said heterocyclic radical also to be bonded via a C$_1$–C$_6$-alkylene bridge to the oxygen atom in the 5'-position of the tetrahydrofuran ring, their preparation and their use against parasites in productive livestock and against insect pests, are described.

19 Claims, No Drawings

COMPOSITION FOR CONTROLLING PARASITES IN PRODUCTIVE LIVESTOCK

The present invention relates to novel 13-spiro-2'-[tetrahydrofuran]milbemycin derivatives of the formula I below, to their preparation, to compositions that contain at least one of these substances as active ingredient, and to their use for controlling ecto- and endo-parasites in productive livestock.

The novel compounds have the general formula I

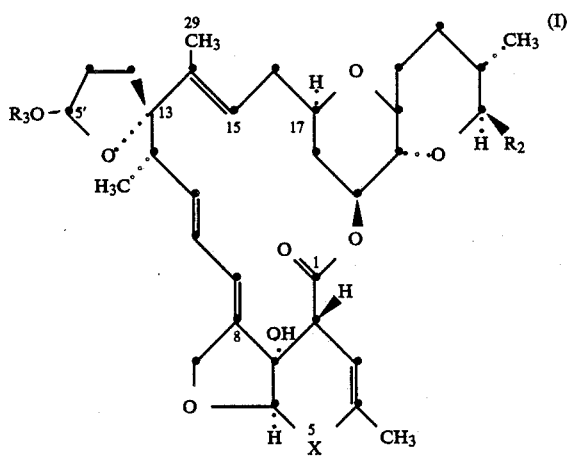

in which

X represents one of the groups —CH(OR$_1$)—, —C(=O)— or —C(=N—OH)—;

R$_1$ represents hydrogen or a OH-protecting group;

R$_2$ represents methyl, ethyl, isopropyl or sec.-butyl or the group —C(CH$_3$)=CH—A in which A represents methyl, ethyl or isopropyl; and R$_3$ represents hydrogen; C$_1$–C$_{10}$-alkyl; C$_1$–C$_{10}$-alkyl substituted by at least one substituent selected from the group consisting of halogen, C$_1$–C$_6$-alkoxy, C$_2$–C$_6$-alkoxyalkoxy, C$_3$–C$_9$-alkoxyalkoxyalkoxy, C$_1$–C$_6$-alkylthio, C$_3$–C$_7$-cycloalkyl, C$_1$–C$_3$-alkyl-substituted C$_3$–C$_7$-cycloalkyl, hydroxy, benzyloxy, C$_1$–C$_6$-acyl and C$_1$–C$_6$-acyloxy, it being possible for each of the above-mentioned radicals representing or containing an alkoxy group to be terminally substituted at a terminal alkoxy group by hydroxy, halogen, C$_1$–C$_6$-acyl or by C$_1$–C$_6$-acyloxy; C$_3$–C$_7$-cycloalkyl; C$_3$C$_7$-cycloalkyl substituted by at least one substituent selected from the group consisting of halogen and C$_1$–C$_3$-alkyl; C$_3$–C$_7$-cycloalkenyl; C$_2$–C$_{10}$-alkenyl; C$_2$–C$_{10}$-alkynyl; a radical selected from the group consisting of C$_2$–C$_{10}$-alkenyl and C$_2$–C$_{10}$-alkynyl, which radical is substituted by halogen, C$_1$–C$_6$-alkoxy or by C$_1$–C$_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, C$_1$–C$_3$-alkyl, C$_1$–C$_3$-haloalkyl, C$_1$–C$_3$-alkoxy, C$_1$–C$_3$-haloalkoxy, C$_1$–C$_3$-alkylthio, nitro and cyano; benzyl substituted by a phenoxy group; or a four- to six-membered heterocyclic radical that has from one to three hetero atoms selected from the group consisting of oxygen, sulphur and nitrogen and that is unsubstituted or is substituted by at least one substituent selected from the group consisting of halogen, C$_1$–C$_3$-alkyl, C$_1$–C$_3$-haloalkyl, C$_1$–C$_3$-alkoxy, C$_1$–C$_3$-haloalkoxy, C$_1$–C$_3$-alkylthio, nitro and cyano, it being possible for the said heterocyclic radical also to be bonded via a C$_1$–C$_6$-alkylene bridge to the oxygen atom in the 5'-position of the tetrahydrofuran ring.

Menthyl groups that come into consideration are those menthyl groups which are derived from o-, m- and p-menthene and can be linked to the oxygen atom located at the C$_5$' atom via one of the unsubstituted ring carbon atoms. 2-methyl-6-isopropylcyclohexyl should be mentioned as a preferred menthyl group. Carveyl is preferably 2-methyl-5-(1-methylvinyl)-2-cyclohexen-2-yl.

The compounds of formula I can be in the form of a mixture of epimers in respect of the C$_5$' carbon atom in the tetrahydrofuran ring. The pure epimers are obtained by means of customary physical separation methods. Hereinafter the two epimers are identified by the letters A and B.

Here and hereinafter, Oh-protecting groups for substituent R$_1$ should be understood as meaning the protective functions customary in organic chemistry. These are especially acyl and silyl groups. Suitable acyl groups are, for example, radicals R$_4$—C(O)— in which R$_4$ represents C$_1$–C$_{10}$-alkyl, C$_1$–C$_{10}$-haloalkyl or a radical selected from the group consisting of phenyl and benzyl that is unsubstituted or is substituted by at least one substituent selected from the group consisting of halogen, C$_1$–C$_3$-alkyl, C$_1$–C$_3$-haloalkyl, C$_1$–C$_3$-alkoxy, C$_1$–C$_3$-haloalkoxy, cyano and nitro and is preferably C$_1$–C$_6$-alkyl, C$_1$–C$_6$-haloalkyl or phenyl that is unsubstituted or is substituted by halogen, C$_1$–C$_3$-alkyl, CF$_3$ or by nitro. A suitable silyl group for R$_1$ is the radical —Si(R$_5$)(R$_6$)(R$_7$) in which R$_5$, R$_6$ and R$_7$ preferably independently of one another, represent C$_1$14 C$_6$-alkyl, benzyl or phenyl and, together with the silicon atom, form, for example, one of the groups trimethylsilyl, thexyldimethylsilyl (thexy=1,1,2-trimethyl-1-propyl: (CH$_3$)$_2$CH—C(CH$_3$)$_2$—), diphenyl-tert.-butylsilyl, bis-(isopropyl)methylsilyl, triphenylsilyl and especially tert.-butyldimethylsilyl. The 5-OH group can also be etherified in benzyl ether or methoxyethoxymethyl ether form or, in accordance with European A-specification No. 185 623, can be bonded to a carbohydrate radical, hereinafter referred to as a sugar radical for the sake of simplicity.

Suitable structural elements that are substituted "by at least one substituent" selected from a specified group of substituents are those which can be derived from compounds that can be prepared according to customary chemical methods. The said structural elements are preferably substituted by from 1 to 3 substituents, there generally being no more than one nitro or cyano group present.

Compounds of formula I in which X represents —CH(OR$_1$)— and R$_1$ represents a protecting group can be converted into the highly active free 5-hydroxy derivatives (X=—CH(OR$_1$)—, R$_1$=H) by simple, for example hydrolytic, removal of the protective function and therefore also have the character of intermediates.

Preferred substituents of phenyl groups are from 1 to 3 halogen atoms, C$_1$–C$_2$-alkyl, C$_1$–C$_2$-alkoxy, C$_1$–C$_2$-alkylthio, C$_1$–C$_2$-haloalkyl or nitro and cyano. Of all the substituents of phenyl groups that contain an alkyl group, those having 1 carbon atom are especially preferred. Where there is more than one substituent, these substituents can be present independently of one another. An α-methylbenzyl group is also to be regarded as an alkyl-substituted benzyl group.

The term "alkyl" on its own or as part of another substituent, depending upon the number of carbon atoms indicated, is to be understood as including, for example, the following radicals: methyl, ethyl, propyl, butyl, pentyl, hexyl, heptyl, octyl, nonyl, and decyl, and also the isomers, such as, for example, isopropyl, isobutyl, tert.-butyl and isopentyl. Haloalkyl represents a mono- to per-halogenated alkyl substituent, such as, for example, $CHCl_2$, $CHF_2$, $CH_2Cl$, $CCl_3$, $CF_3$, $CH_2F$, $CH_2CH_2Cl$ and $CHBr_2$, preferably $CF_3$. Halogen shoud be understood here and hereinafter as being fluorine, chlorine, bromine or iodine, preferably fluorine, chlorine or bromine. Alkenyl represents an aliphatic hydrocarbon radical characterised by at least one C=C double bond, such as, for example, vinyl, propen-1yl, allyl, buten-1-yl, buten-2-yl, and buten-3-yl.

$C_2$–$C_6$-alkoxyalkoxy represents an alkoxy radical of which the carbon chain consists of up to 6 carbon atoms and is interrupted by an oxygen atom, for example $OCH_2OCH_3$, $OCH_2CH_2OCH_3$, $OCH_2OC_2H_5$, $OCH_2CH_2CH_2OC_3H_7$ or $OC(CH_3)_2OC_2H_5$. $C_3$–$C_9$-alkoxyalkoxyalkoxy consists of an alkoxy radical of which the carbon chain consists of from 3 to 9 carbon atoms and is interrrupted in two places by an oxygen atom, for example $OCH_2OCH_2OCH_3$, $OC_2H_4OC_2H_4OC_2H_5$ or $OCH_2CH_2OCH_2CH_2OCH_2CH_2CH_3$. Alkynyl represents, for example, ethynyl, propyn-1-yl, propargyl or butyn-1-yl. Cycloalkyl represents, for example, cyclopropyl, cyclobutyl, cyclopentyl, cyclohexyl, cycloheptyl or cyclooctyl. Of the alkyl groups substituted by benzyloxy, those are preferred which contain from 1 to 3 carbon atoms in the alkyl moiety and are monosubstituted by benzyloxy, especially 2-benzyloxyethyl. Acyl as $R_3$ or as part of $R_3$ preferably represents the alkanoyl radical derived from a straight-chain or branched alkanoic acid, for example $CH_3CO$, $C_2H_5CO$, i-$C_3H_7CO$, n-$C_3H_7CO$, n-$C_4H_9$-CO or tert.-butylCO, in which the alkyl radicals may also be halogenated, such as, for example, as indicated above for haloalkyl. Cycloalkenyl represents one of the above cycloalkyl radicals but contains at least one double bond and does not have aromatic character.

Of the four-membered heterocyclic rings, special preference is given to those which contain a hereto atom from the group consisting of oxygen, sulphur and nitrogen and are saturated. Typical examples are:

Typical five-membered heterocyclic rings are: furan, thiophene, pyrrole, isoxazole, isothiazole, furazan, imidazole, 1,2,4-triazole, 1,2,3-triazole, pyrazole, pyrroline, oxazole, thiazole, thiadiazoles, pyrazoline, thiazoline, pyrazolidine, pyrrolidine, oxazolidine, thiazolidine, oxadiazole, imidazoline, imidazoline, pyrazolidine, tetrahydrofuran; and typical six-membered heterocyclic rings are pyridine, pyridazine, pyrimidine, pyrazine, thiazine, thiadiazines, pyrans, piperidine, piperazine, morpholine, perhydrothiazine, dioxan and their partially hydrogenated or partially saturated homologues. The heterocyclic radical is generally bonded via a carbon atom, preferably the carbon atom adjacent to a hereto atom, to the rest of the molecule.

Compounds of formula I in which X represents —$CH(OR_1)$— or —$C(=N$—$OH)$— in which $R_1$ represents hydrogen or a OH-protecting group, are preferred, especially those compounds of formula I in which X represents —$CH(OR_1)$— and $R_1$ represents hydrogen. Acyl and silyl groups as $R_1$ are generally to be understood as protecting groups.

Compounds of formula I in which $R_2$ represents methyl, ethyl, isopropyl or sec.-butyl, especially ethyl or methyl, preferably ethyl, are preferred.

Compounds in which $R_2$ represents sec.-butyl shall here and hereinafter also be considered as milbemycin derivatives although according to conventional classification they are derived from avermectin derivatives. Avermectin-aglycones (with an OH group in the 13α-position) can, however, be converted in accordance with US-PS 4 173 571 into milbemycin homologues.

In naturally occurring milbemycins ($R_1$=H; $R_2$=$CH_3$, $C_2H_5$ or iso-$C_3H_7$) the 13-position is always occupied only by hydrogen. In avermectins, however, the 13-position is occupied by an α-L-oleandrosyl-α-L-oleandrose radical which is linked via oxygen in the α-configuration to the macrolide molecule. Avermectins also differ structurally from milbemycins by a 23-OH group or $\Delta^{22,23}$ double bond and generally by a substituent $R_2$=sec.$C_4H_9$. By hydrolysing the sugar radical of avermectins it is readily possible to obtain the corresponding avermectin-aglycones that have an allylic 13α-hydroxy group. The avermectin-aglycones can be converted into the milbemycin homologues as indicated above. In the milbemycin derivatives of the present application, the $\Delta^{22,23}$ double bond is always in hydrogenated form.

The following sub-groups of compounds of formula I are especially preferred because of their pronounced parasiticidal and insecticidal action:

Group Ia: Compounds of formula I in which
X represents —$CH(OR_1)$— or —$C(=N$—$OH)$—, preferably —$CH(OR_1)$—;
$R_1$ represents hydrogen or a OH-protecting group;
$R_2$ represents methyl, ethyl, isopropyl or sec.-butyl; and
$R_3$ represents hydrogen; $C_1$–$C_{10}$-alkyl; $C_1$–$C_{10}$ alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, hydroxy and $C_1$–$C_6$-acyl, it being possible for each of the above mentioned radicals representing or containing an alkoxy group to be terminally substituted at a terminal alkoxy group by hydroxy, halogen, $C_1$–$C_6$-acyl or by $C_1$–$C_6$-acyloxy; an ethyl group substituted by benzyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$alkoxy or by $C_1$–$C_6$- acyloxy; 1-adamantylmethyl; methyl; carveyl; phenyl; benzyl; naphthyl; a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano; benzyl substituted by a phenoxy group; or a four- to six-membered heretocyclic radical that has from one to three hetero atoms selected from the group consisting of oxygen, sulphur and nitrogen and that is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano, it being possible for the said heterocyclic radical also to be bonded via a $C_1$–$C_6$-alkylene bridge to the oxygen atom in the 5'-position of the tetrahydrofuran ring.

Group Ib: Compounds of formula I in which
X represents —CH($OR_1$)—;
$R_1$ represents hydrogen or a OH-protecting group;
$R_2$ represents methyl, ethyl, isopropyl or sec.-butyl; and
$R_3$ represents hydrogen; $C_1$–$C_{10}$-alkyl; $C_1$–$C_{10}$-alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, hydroxy and $C_1$–$C_6$-acyl, it being possible for each of the above mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$-alkoxy or by $C_1$–$C_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano; or a four- to six-membered heterocyclic radical that has from one to three hereto atoms selected from the group consisting of oxygen, sulphur and nitrogen and that is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano, it being possible for the said heterocyclic radical also to be bonded via a $C_1$–$C_6$-alkylene bridge to the oxygen atom in the 5'-position of the tetrahydrofuran ring.

Group Ic: Compounds of formula I in which X represents —CH($OR_1$)— and $R_1$ represents hydrogen, $R_4$—C(O)— or —Si($R_5$)($R_6$)($R_7$); wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_6$-alkyl, benzyl or phenyl; $R_2$ represents methyl, ethyl, isopropyl or sec.-butyl; and $R_3$ represents hydrogen, $C_1$–$C_5$-alkyl; $C_1$–$C_5$-alkyl substituted by at least one substituent selected from the group consisting of halogen, $C_1$–$C_3$-alkoxy, $C_2$–$C_6$-alkoxyalkoxy, $C_3$–$C_9$-alkoxyalkoxyalkoxy, $C_1$–$C_3$-alkylthio, $C_3$–$C_7$-cycloalkyl, hydroxy and $C_1$–$C_6$-acyl, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of fluorine, chlorine, bromine and methyl; $C_2$–$C_6$-alkenyl; $C_2$–$C_6$-alkynyl; a radical selected from the group consisting of $C_2$–$C_6$-alkenyl and $C_2$–$C_6$-alkynyl, which radical is substituted by fluorine, chlorine, bromine, $C_1$–$C_3$-alkoxy or by $C_1$–$C_6$-acyloxy; phenyl; benzyl; α-naphthyl; β-naphthyl; a radical selected from the group consisting of phenyl, benzyl, α-naphthyl and β-naphthyl, which radical is substituted by at least one substituent selected from the group consisting of fluorine, chlorine, bromine, methyl, methoxy, $CF_3$, $CF_3O$, $CH_3S$, nitro and cyano; or a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, $CF_3$, $CH_3O$, $CF_3O$, $CH_3S$, nitro and cyano, it being possible for the said heterocyclic radical also to be bonded via a $C_1$–$C_6$-alkylene bridge to the oxygen atom in the 5'-position of the tetrahydrofuran ring.

Group Id: Compounds of formula I in which X represents —CH($OR_1$)— and $R_1$ represents hydrogen, $R_4$—C(O)— or —Si($R_5$)($R_6$)($R_7$); wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$-alkyl, benzyl or phenyl; $R_2$ represents methyl, ethyl, isopropyl or sec.-butyl; and $R_3$ represents $C_1$–$C_5$-alkyl, or $C_1$–$C_5$-alkyl substituted by at least one substituent selected from the group consisting of halogen, $C_1$–$C_3$-alkoxy, $C_2$–$C_6$-alkoxyalkoxy, $C_3$–$C_9$-alkoxyalkoxyalkoxy, $C_1$–$C_3$-alkylthio, $C_3$–$C_7$-cycloalkyl, hydroxy and $C_1$–$C_6$-acyl, it being possible for each of the above-mentioned radicals representing or containing an alkoxy group to be terminally substituted at a terminal alkoxy group of hydroxy, halogen, $C_1$–$C_6$-acyl or by $C_1$–$C_6$-acyloxy.

Group Ie: Compounds of formula I in which X represents —CH($OR_1$)— and $R_1$ represents hydrogen, $R_4$—C(O)— or —Si($R_5$)($R_6$)($R_7$); wherein $R_4$ represents $C_1$–$C_6$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$alkyl, benzyl or phenyl; $R_2$ represents methyl, ethyl, isopropyl or sec.-butyl; and $R_3$ represents $C_3$–$C_7$-cycloalkyl; $C_3$–$C_7$-cycloalkyl substituted by at least one substituent selected from the group consisting of fluorine, chlorine, bromine and methyl; $C_2$–$C_6$-alkenyl; $C_2$–$C_6$-alkynyl; a radical selected from the group consisting of $C_2$–$C_6$-alkenyl and $C_2$–$C_6$-alkynyl, which radical is substituted by fluorine, chlorine, bromine, $C_1$–$C_3$-alkoxy or by $C_1$–$C_6$-acyloxy; phenyl; benzyl; α-naphthyl; β-naphthyl; a radical selected from the group consisting of phenyl, benzyl, α-naphthyl and β-naphthyl, which radical is substituted by at least one substituent selected from the group consisting of fluorine, chlorine, bromine, methyl, methoxy, $CF_3$, $CF_3O$, $CH_3S$, nitro and cyano; or a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, $CF_3$, $CH_3O$, $CF_3O$, $CH_3S$, nitro and cyano, it being possible for the said heterocyclic radical also to be bonded via a $C_1$–$C_6$-alkylene bridge to the oxygen atom in the 5'position of the tetrahydrofuran ring.

Group If: Compounds of formula I in which X represents —$CH(O_1)$— and $R_1$ represents hydrogen, $R_4$—C(O)— or —$Si(R_5)(R_6)(R_7)$; wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$-alkyl, benzyl or phenyl; $R_2$ represents methyl, ethyl, isopropyl or sec.-butyl; and $R_3$ represents phenyl, benzyl, α-naphthyl, β-naphthyl or a radical selected from the group consisting of phenyl, benzyl, α-naphthyl and β-naphthyl, which radical is substituted by at least one substituent selected from the group consisting of fluorine, chlorine, bromine, methyl, methoxy, $CF_3$, $CF_3O$, $CH_3S$, nitro and cyano.

Group Ig: Compounds of formula I in which X represents —$CH(OR_1)$— and $R_1$ represents hydrogen, $R_4$—C(O)— or —$Si(R_5)(R_6)(R_7)$; wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$-alkyl, benzyl or phenyl; $R_2$ represents methyl, ethyl, isopropyl or sec.-butyl; and $R_3$ represents $C_2$–$C_6$-alkenyl, $C_2$–$C_6$-alkynyl, or a radical selected from the group consisting of $C_2$–$C_6$-alkenyl and $C_2$–$C_6$-alkynyl, which radical is substituted by fluorine, chlorine, bromine, $C_1$–$C_3$alkoxy or by $C_1$–$C_6$-acyloxy.

Group Ih: Compounds of formula I in which X represents —$CH(OR_1)$— and $R_1$ represents hydrogen, $R_4$—C(O)— or —$Si(R_5)(R_6)(R_7)$; wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$, benzyl or phenyl; $R_2$ represents methyl, ethyl, isopropyl or sec.-butyl; and $R_3$ represents a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, $CF_3$, $CH_3O$, $CF_2O$, $CH_3S$, nitro and cyano, it being possible for the said heterocyclic radical also to be bonded via a $C_1$–$C_6$-alkylene bridge to the oxygen atom in the 5'-position of the tetrahydrofuran ring.

Group Ii: Compounds of formula I in which X represents —$CH(OR_1)$— and $R_1$ represents hydrogen, $R_4$—C(O)— or —$Si(R_5)(R_6)(R_7)$; wherein $R_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and $R_5$, $R_6$ and $R_7$, independently of one another, represent $C_1$–$C_4$-alkyl, benzyl or phenyl; $R_2$ represents methyl, ethyl, isopropyl or sec.-butyl; and $R_3$ represents an unsaturared or preferably saturated four-membered heterocyclic radical haivng a hetero atom selected from the group consisting of oxygen, nitrogen and sulphur, or represents furan, thiophene, pyrrole, isoxazole, isothiazole, furazan, imidazole, 1,2,4-triazole, 1,2,3-triazole, pyrazole, pyrroline, oxazole, thiazole, thiadiazoles, pyrazoline, thiazoline, pyrazolidine, pyrrolidine, oxazolidine, thiazolidine, oxadiazole, imidazoline, imidazolidine, pyrazolidine, tetrahydrofuran, pyridine, pyridazine, pyrimidine, pyrazine, thiazine, thiadiazines, pyrans, piperidine, piperazine, morpholine, perhydrothiazine or dioxan, it being possible for the said heterocyclic radical also to be bonded via a C1–C4-alkylene bridge to the oxygen atom in the 5'-position of the tetrahydrofuran ring.

Group Ik: Compounds of formula I in which X represents —$CH(OR_1)$— and $R_1$ represents hydrogen or —$Si(R_5)(R_6)(R_7)$; wherein $R_5$, $R_6$ and $R_7$, independently of one another, represent $C_1$–$C_6$-alkyl; $R_2$ represents methyl, ethyl, isopropyl or sec.-butyl; and $R_3$ represents $C_1$–$C_{10}$-alkyl; $C_1$–$C_{10}$-alkyl substituted by at least one substituent selected from the group consisting of C1–C4-alkoxy, $C_1$–$C_3$-alkylthio, $C_1$–$C_6$-alkanoyloxy, benzyloxy and $C_3$–$C_7$-cycloalkyl; $C_3$–$C_7$-cycloalkyl; phenyl; benzyl; or a radical selected from the group consisting of phenyl and benzyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy and $C_1$–$C_3$-alkylthio.

Group Il: Compounds of formula I in which X represents —$CH(OR_1)$— and $R_1$ represents hydrogen or —$Si(R_5)(R_6)(R_7)$; wherein $R_5$, $R_6$ and $R_7$, independently of one another, represent $C_1$–$C_6$-alkyl; $R_2$ represents methyl, ethyl, isopropyl or sec.-butyl; and $R_3$ represents hydrogen; $C_1$–$C_{10}$-alkyl; $C_1$–$C_{10}$-alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, hydroxy and $C_1$–$C_6$-alkanoyloxy, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$-alkoxy or by $C_1$–$C_6$-acyloxy, 1-adamantylmethyl; menthyl; carveyl; phenyl; benzyl; naphthyl; or a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano.

Group Im: Compounds of formula I in which X represents —$CH(OR_1)$— and $R_1$ represents hydrogen, trimethylsilyl, tert.-butyldimethylsilyl or thexyldimethylsilyl; $R_2$ represents methyl, ethyl, isopropyl or sec.-butyl; and $R_3$ represents hydrogen; $C_1$–$C_{10}$-alkyl; $C_1$–$C_{10}$-alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, hydroxy and $C_1$–$C_6$-alkanoyloxy, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_2$–$C_{10}$-alkenyl; $C_2C_{10}$-alkynyl; 1-adamantylmethyl; methyl; carveyl; phenyl; benzyl; naphthyl; or a radical selected from the group consisting of phenyl and benzyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano.

Group In: Compounds of formula I in which X represents —CH($R_1$)— in which $R_1$ represents hydrogen or tert.-butyldimethylsilyl, or —C(=N—OH)—; $R_2$ represents methyl or preferably ethyl, and $R_3$ represents hydrogen, $C_1$–$C_8$-alkyl, $C_1$–$C_5$-alkyl that is substituted by from 1 to 3 halogen atoms, preferably chlorine or bromine atoms, or is monosubstituted by $C_1$–$C_3$-alkoxy, $C_2$–$C_6$-alkoxy that is interrupted by an oxygen atom and is unsubstituted or is terminally monosubstituted at the terminal alkoxy group by hydroxy or by halogenated, preferably chlorinated, $C_1$–$C_3$-alkanoyloxy, $C_1$–$C_3$-alkylthio, $C_3$–$C_7$-cycloalkyl or hydroxy, $C_2$–$C_4$-alkyl that is monosubstituted by unsubstituted or halogenated, preferably chlorinated, $C_1$–$C_3$-alkanoyloxy or by benzyloxy, $C_3$–$C_7$-cycloalkyl that is unsubstituted or mono- or di-substituted by $C_1$–$C_3$-alkyl, 1-adamantylmethyl, phenyl, benzyl that is unsubstituted, monosubstituted by phenoxy or substituted by from 1 to 3 $C_1$–$C_3$-alkoxy groups, α-methylbenzyl, or a heterocyclic radical selected from the group consisting of oxetanyl and furyl that is bonded via $C_1$–$C_3$-alkyl and is unsubstituted or is substituted by methyl.

Group Io: Compounds of formula I in which X represents —CH($R_1$) and $R_1$ represents hydrogen or tert.-butyldimethylsilyl; $R_2$ represents ethyl; and $R_3$ represents hydrogen, $C_1$–$C_8$-alkyl, $C_1$–$C_5$-alkyl that is substituted by from 1 to 3 halogen atoms, preferably chlorine or bromine atoms, or is monosubstituted by $C_1$–$C_3$-alkoxy, $C_2$–$C_6$-alkoxy that is interrupted by an oxygen atom and is unsubstituted or is terminally monosubstituted at the terminal alkoxy group by hydroxy or by halogenated, preferably chlorinated, $C_1$–$C_3$-alkanoyloxy, $C_1$–$C_3$-alkylthio, $C_3$–$C_7$-cycloalkyl, or hydroxy, ethyl that is monosubstituted by acetoxy, chloroacetoxy or by benzyloxy, $C_3$–$C_7$-cycloalkyl that is unsubstituted or is mono- or di-substituted by $C_1$–$C_3$-alkyl, 1-adamantylmethyl, phenyl, benzyl that is unsubstituted, monosubstituted by phenoxy or substituted by from 1 to 3 $C_1$–$C_3$-alkoxy groups, α-methylbenzyl, or a heterocyclic radical selected from the group consisting of oxetanyl and furyl that is bonded via $C_1$–$C_3$-alkyl and is unsubstituted or substituted by methyl.

Group Ip: Compounds of formula I in which X represents —CH($OR_1$)— and $R_1$ represents hydrogen or tert.-butyldimethylsilyl; $R_2$ represents ethyl; and $R_3$ represents hydrogen, $C_1$–$C_8$-alkyl, 2,2,2-tribromoethyl, 2,2-bis(chloromethyl)-propyl, 3-chloro-2,2-dimethylpropyl, 2-ethoxyethyl, 2-(2-methoxyethoxy)-ethyl, 2-[2-(2-hydroxyethoxy)-ethoxy]-ethyl, 2-{2-[(2-chloroacetoxy)-ethoxy]-ethoxy}-ethyl, 2-methylthioethyl, cyclobutylmethyl, cyclohexylmethyl, 2-hydroxyethyl, benzyloxyethyl, 2-acetoxyethyl, 2-(chloroacetoxy)-ethyl, cyclopentyl, cyclohexyl, cycloheptyl, 2-methyl-6-isopropylcyclohexyl, 1-adamantylmethyl, phenyl, benzyl, 3-phenoxybenzyl, 3,4-dimethoxybenzyl, α-methylbenzyl, (3-methyloxetan-3-yl)-methyl or furfuryl.

Group Iq: Compounds of formula I in which X represents —CH($OR_1$)— and $R_1$ represents hydrogen or tert.-butyldimethylsilyl; $R_2$ represents ethyl; and $R_3$ represents $C_1$–$C_5$-alkyl, $C_2$–$C_4$-alkyl that is substituted by from 1 to 3 halogen atoms, especially bromine atoms, or is monosubstituted by $C_1$–$C_3$-alkoxy, $C_2$–$C_6$-alkoxy that is interrupted by an oxygen atom and is unsubstituted or is terminally monosubstituted at the terminal alkoxy group by hydroxy or halogenated, especially chlorinated, $C_1$–$C_3$-alkanoyl, $C_1$–$C_3$-alkylthio, or hydroxy, 2-acetoxyethyl, cyclohexyl that is unsubstituted or mono- or di-substituted by $C_1$–$C_3$-alkyl, 1-adamantylmethyl, benzyl, or a heterocyclic radical selected from the group consisting of oxetanyl and furyl that is bonded via $C_1$–$C_3$-alkyl and is unsubstituted or substituted by methyl.

Group Ir: Compounds of formula I in which X represnts —CH($OR_1$)— and $R_1$ represents hydrogen or tert.-butyldimethylsilyl; $R_2$ represents ethyl; and $R_3$ represents $C_1$–$C_5$-alkyl, 2,2,2-tribromomethyl, 2-ethoxyethyl, 2-(2-methoxyethoxy)-ethyl, 2-[2-(2-hydroxyethoxy)-ethoxy]-ethyl, 2-{2-[(2-chloroacetoxy)-ethoxy]-ethoxy}-ethyl, 2-methylthioethyl, 2-hydroxyethyl, 2-acetoxyethyl, cyclohexyl, 2-methyl-6-isopropylcyclohexyl, 1-adamantylmethyl, benzyl, (3-methyloxetan-3-yl)-methyl or furfuryl.

Group Is: Compounds of formula I in which X represents —CH($OR_1$)— and $R_1$ represents hydrogen; $R_2$ represents ethyl; and $R_3$ represents $C_4$–$C_5$-alkyl, $C_4$–$C_6$-cycloalkyl, $C_4$–$C_6$-cycloalkyl bonded via methyl, or phenyl, benzyl or α-methylbenzyl. Representatives of this group that are of special interest are: milbemycin $A_4$-13-spiro-2'-[5'-(2''-methylbutoxy)-tetrahydrofuran] and milbemycin $A_{14}$-13-spiro-2'-[5'-(1'''-methylpropoxy)-tetrahydrofuran].

Group It: Compounds of formula I in which X represents —C(=N—H)—; $R_2$ represents methyl or preferably ethyl; and $R_3$ represents $C_1$-$C_5$-alkyl, $C_1$-$C_3$-alkyl that is substituted by $C_1$-$C_3$-alkoxy, or $C_3$-$C_7$-cycloalkyl.

Within groups Ia to Im, those representatives of formula I in which $R_2$ represents methyl or ethyl, especially ethyl, are preferred.

Preferred individual substances of formula I are, for example:

milbemycin $A_{14}$-13-spiro-2'-[5'-(2''-ethoxyethoxy)-tetrahydrofuran], milbemycin $A_4$-13-spiro-2'-[5'-(2'',2''-dimethylpropoxy)-tetrahydrofuran], milbemycin $A_4$-13-spiro-2'-[5'-cyclohexyloxytetrahydrofuran], milbemycin $A_4$-13-spiro-2'-[5'-benzyloxytetrahydrofuran], milbemycin $A_4$-13-spiro-2'-[5'-{2''-(2'''-methoxyethoxy)-ethoxy}-tetrahydrofuran], milbemycin $A_4$-13-spiro-2'-[5'-{2''-(2'''-(hydroxymethoxy)-ethoxy)-ethoxy}-tetrahydrofuran], milbemycin $A_4$-13-spiro-2'-[5'-{2''-(2'''-(2''''-(chloroacetoxy)-ethoxy)-ethoxy)-ethoxy}-tetrahydrofuran], milbemycin $A_4$-13-spiro-2'-[5'-methoxytetrahydrofuran], and milbemycin $A_4$-13-spiro-2'-[5'-(2''-hydroxyethoxy)-tetrahydrofuran].

Other individual substances that are worthy of mention are:

milbemycin $A_4$-13-spiro-2'-[5'-(2''-methoxybutoxy)-tetrahydrofuran], and milbemycin $A_4$-13-spiro-2'-[5'-(1''-methylpropoxy)-tetrahydrofuran].

Likewise, the analogous representatives of formula I that are protected in the 5-position by a 5-0-tert.-butyldimethylsilyl group are also preferred.

The present invention relates also to processes that enable an additional, spiro-linked tetrahydrofuran ring to be introduced specifically into the 13-position of derivatives of milbemycin, 13-deoxy-22,23-dihydroavermectin-aglycone or 23-deoxy-antibiotics S541 in order thus to obtain highly active novel parasiticides of formula I. The invention relates also to intermediates obtainable according to the processes.

Formula I includes the compounds of the formulae Ia, Ib and Ic:

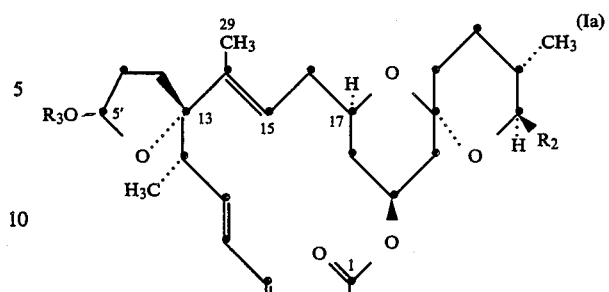
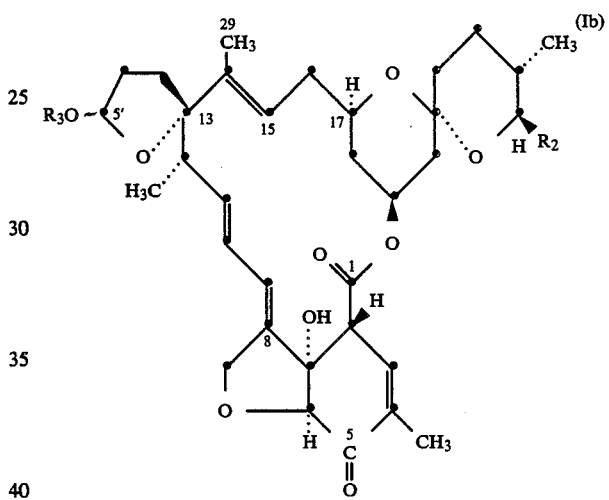
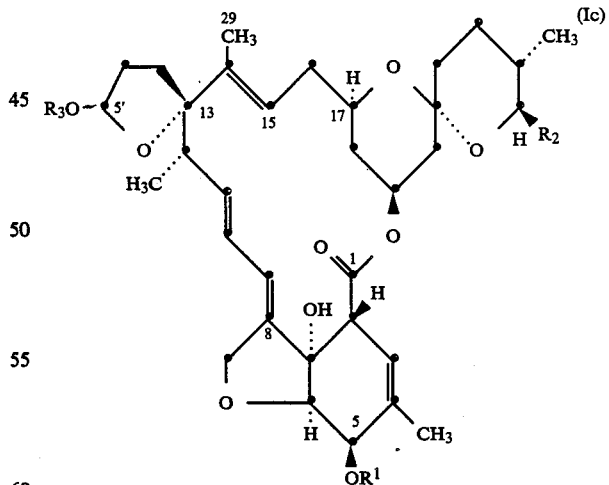

in which $R_1$, $R_2$ and $R_3$ have the meanings given for formula I and which can be prepared according to the methods described below.

The preparation of the oximes [X=—C(=N—OH)—] within the scope of formula I, and therefore of the compounds of formula Ia, is effected by reacting a derivative of formula Ib with hydroxylamine or a salt thereof, preferably a mineral acid salt thereof, especially the hydrochloride. The reaction is advantageously carried out in a suitable solvent, for example a lowr alkanol, such as methanol, ethanol, propanol; an ethereal compound, such as tetrahydrofuran or dioxan; an aliphatic carboxylic acid, such as acetic acid or propionic acid; water or in mixtures of these solvents with one another or with other customary inert solvents. The reaction temperatures may vary within wide ranges. The reaction is advantageously carried out, for example, within a range of from +0° C. to +100° C. If hydroxylamine is used in the form of one of its salts, for example in hydrochloride form, it is advantageous if, to bind the acid (for example HCl), one of the bases customary for such purposes is added and the operation is optionally carried out in the presence of a water binder, for example a molecular sieve. Suitable bases are organic and inorganic bases, for example tertiary amines such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and hydrogen carbonates of alkali metals and alkaline earth metals (CaO, BaO, NaOH, KOH, NaH, Ca(OH)$_2$, KHCO$_3$, NaHCO$_3$, Ca(HCO$_3$)$_2$, K$_2$CO$_3$, Na$_2$CO$_3$), and also alkali metal acetates, such as CH$_3$COONa or CH$_3$COOK. Furthermore, alkali metal alcoholates, such as C$_2$H$_5$ONa, n—C$_3$H$_7$ONa etc., are also suitable. Triethylamine is preferred. The oximation is most advantageously carried out with hydroxylamine hydrochloride in pyridine.

The derivatives of formula Ib can be prepared from the corresponding free 5-hydroxy derivatives of formula Ic by mild oxidation, for example with brownstone (MnO$_2$), CrO$_3$/pyridine or by Oppenauer oxidation. The reaction can be carried out in a solvent, such as, for example, a representative of the ethereal compounds or of the halogenated hydrocarbons or in mixtures of these compounds with one another, but especially advantageously in dichloromethane.

To prepare compounds of formula Ic, the process according to the invention is as follows: a compound of formula II is reacted in the presence of an acid catalyst in an inert solvent with a compound of formula III:

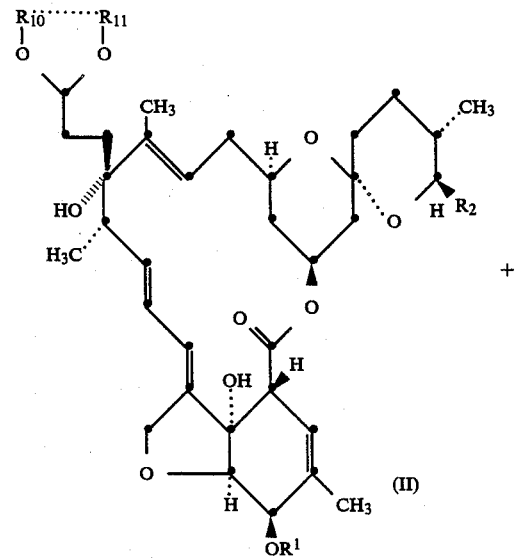

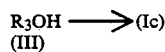

in which the substituents R$_1$, R$_2$ and R$_3$ have the meanings given under formula I and R$_{10}$ and R$_{11}$, independently of one another, represent C$_1$–C$_6$-alkyl or form a C$_2$–C$_{10}$-alkylene bridge, and, if desired, the resulting compound of formula Ic

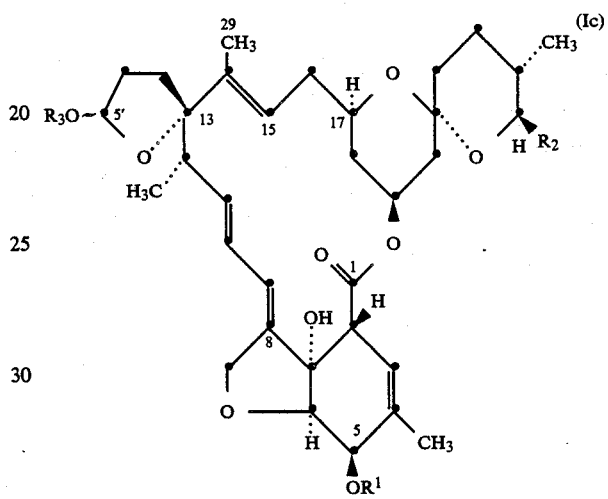

in which R$_1$, R$_2$ and R$_3$ have the meanings given for formula I, is converted by mild oxidation into a corresponding compound of formula Ib

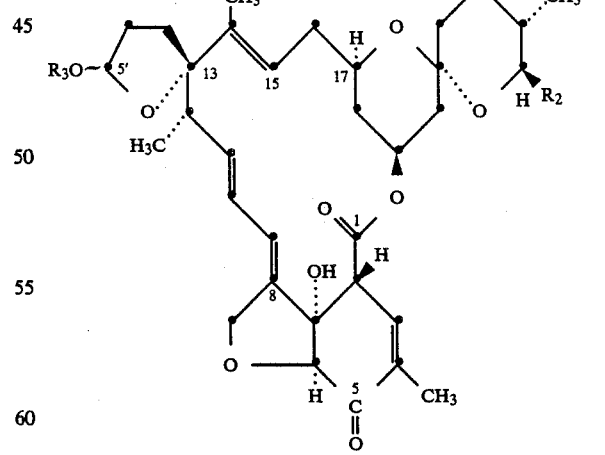

in which R$_2$ and R$_3$ have the meanings given for formula Ic, and, if desired, the compound of formula Ib is converted by reaction with hydroxylamine or a salt thereof into the corresponding compound of formula Ia

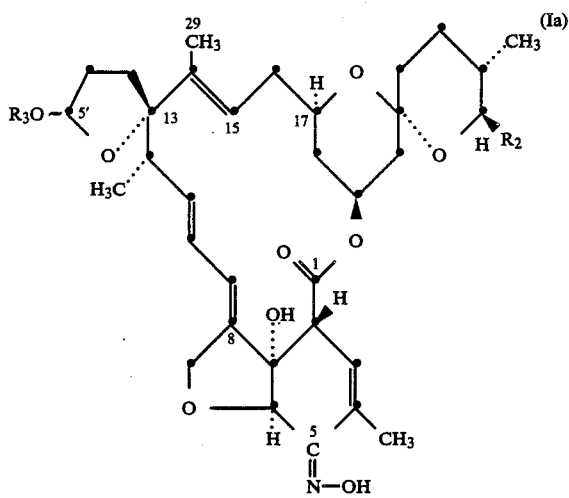

in which $R_2$ and $R_3$ have the meanings given for formula Ib.

The compounds of formula II are novel and have the character of intermediates. Their structure makes them especially suitable for the preparation of active ingredients of formula I. The compounds of formula II therefore form part of the present invention. For the preparation of process products according to the invention it is preferable to use those starting materials of formula II which result in the compounds, especially the individual compounds of the formula I, described above as being especially preferred.

The reaction of the preparation of compounds of formula Ic is generally carried out at temperatures of from $-30°$ C. to $+70°$ C., preferably from $-10°$ C. to $+50°$ C. The reaction is advantageously carried out in the presence of an inert solvent or solvent mixture. Suitable solvents for this purpose are, for example, aliphatic and aromatic hydrocarbons such as benzene, toluene, xylenes, petroleum ether, hexane; halogenated hydrocarbons such as chlorobenzene, methylene chloride, ethylene chloride, chloroform, carbon tetrachloride, tetrachloroethylene; ether and ethereal compounds such as dialkyl ethers (diethyl ether, diisopropyl ether, tert.-butylmethyl ether etc.), anisole, dioxan, tetrahydrofuran; and mixtures of such solvents with one another.

The compound of formula III is generally used in excess. The compounds of formula III are known or can be prepared analogously to known processes.

Suitable acid catalysts are, for example, carboxylic acids such as oxalic acid and especially sulphonic acids such as methanesulphonic acid, p-toluenesulphonic acid, camphor-10-sulphonic acid and salts thereof with tert.-amines, such as, for example, pyridinium p-toluenesulphonate.

Compounds of formula Ic are obtained in the form of mixtures of epimers in respect of C5'. The pure epimers can be obtained therefrom by means of a physical separation operation. Suitable physical separation operations are, for example, column chromatography, flash chromatography, thick-layer chromatography, HPLC and fractional crystallisation.

Compounds of formula Ic can, however, also be prepared from other compounds of formula Ic by suitable reactions.

The preparation of compounds of formula II likewise forms part of the present invention and is effected by reacting a compound of formula IV in an inert solvent with a Grignard reagent of formula V:

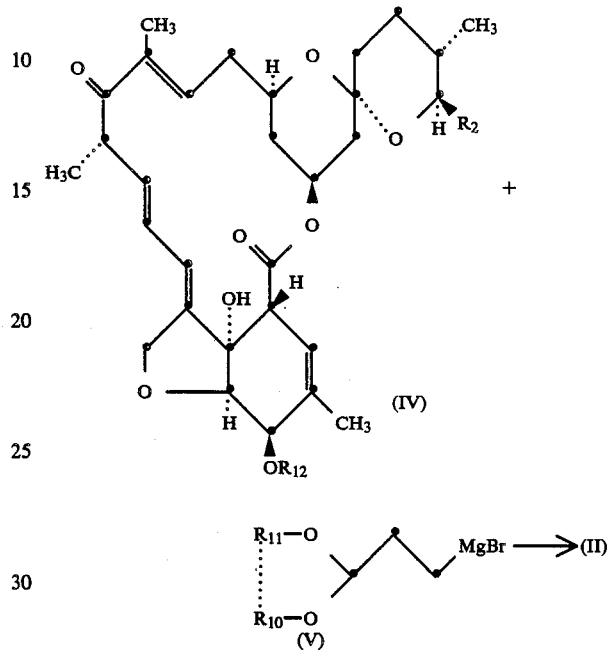

in which $R_2$ has the definition given under formula I, $R_{10}$ and $R_{11}$, independently of one another, represent $C_1$–$C_6$-alkyl or together form a $C_2$–$C_{10}$-alkylene bridge, and $R_{12}$ represents hydrogen or a silyl group as indicated, for example, under formula I.

The reaction is generally carried out at temperatures of from $-80°$ to $+70°$ C., preferably from $-50°$ to $+50°$ C. The reaction is advantageously carried out in the presence of an inert solvent or solvent mixture. Suitable solvents for this purpose are, for example, aliphatic and aromatic hydrocarbons such as benzene, toluene, xylenes, petroleum ether, hexane; ether and etheral compounds such as dialkyl ethers (diethyl ether, diisopropyl ether, tert.-butylmethyl ether etc.), anisole, dioxan, tetrahydrofuran; and mixtures of such solvents with one another.

The Grignard reagents of formula V can be obtained in solution by reaction of the corresponding bromides with magnesium in one of the above-mentioned solvents and can be used further directly without it being necessary to isolate and purify them beforehand.

The compounds of formula IV are known or can be prepared analogously to known methods. For example, compounds of formula IV can be prepared according to the process described in EP 180 539 and EP 184 989, or analogously thereto, as follows: in a first step, compounds of formula VI

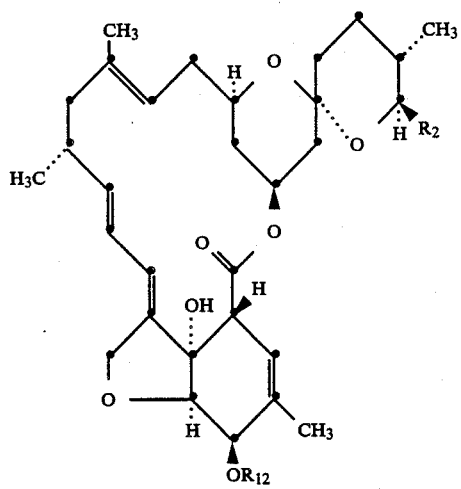 (VI)

in which $R_2$ has the definition given for formula I and $R_{12}$ has the definition given for formula IV, are converted with peracids into the 14,15-epoxides of formula VII:

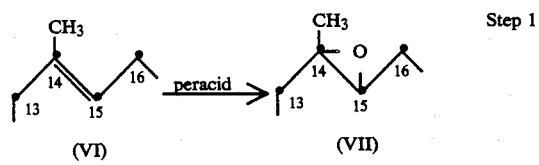

and the 14,15-epoxides of formula VII are then reacted with the aid of a special complex reagent to form 15-hydroxy compounds of formula VIII:

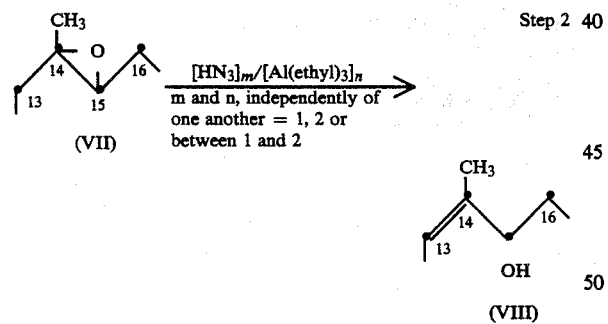

In a further step, the 15-hydroxy compounds of formula VIII are then reacted with chromate, halochromate or dichromate ions, especially with pyridinium dichromate, the starting compound of formula VIII preferably being a compound in which the 5-OH group is protected and can be, for example, in the form of a 5-silyloxy group:

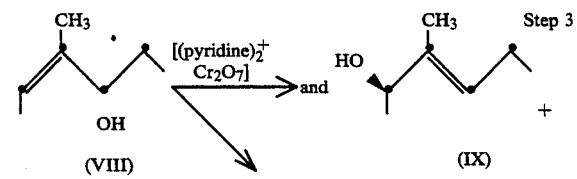

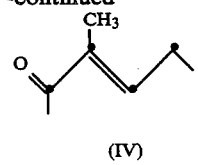 (IV)

there also being formed, in addition to the desired 13-hydroxymilbemycins of formula IX, 13-oxo compounds which can be separated from one another by known methods.

The majority of the described reactions are advantageously carried out under a protective gas, such as, for example, nitrogen or argon.

The compounds of formula VI are known or can be prepared from the known compounds analogously to known processes.

The 13-oxo derivatives of formula IV can be obtained from the 13β-hydroxy derivatives of formula IX by oxidation with dimethyl sulphoxide (DMSO)/oxalyl chloride. The reaction is preferably carried out at temperatures of from −60° C. to room temperature. Suitable solvents are DMSO itself and also aromatic hydrocarbons such as benzene, toluene, xylenes and chlorinated hydrocarbons, such as, for example, dichloromethane. The operation is preferably carried out with the addition of a base, such as, for example, triethylamine.

The known compounds include milbemycins of formula M:

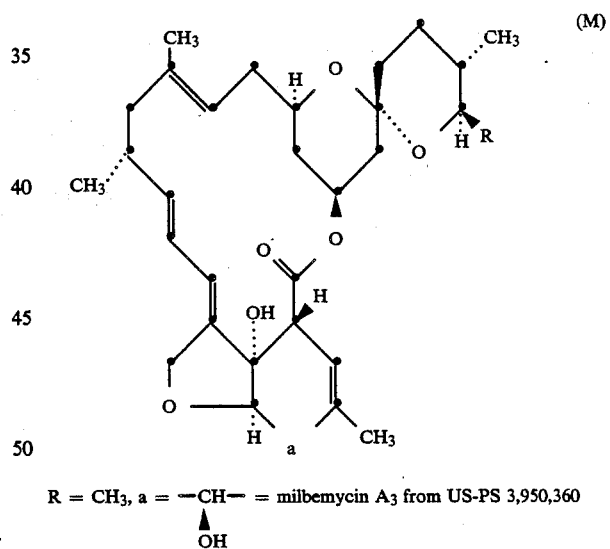

R = $CH_3$, a = —CH— = milbemycin $A_3$ from US-PS 3,950,360
                      OH R = $C_2H_5$, a = —CH— = milbemycin $A_4$ from US-PS 3,950,360
                      OH R = $isoC_3H_7$, a = —CH— = milbemycin D from
                          US-PS 4,346,171
                    OH R = sek.$C_4H_9$, a = —CH— =
                   OH
13-deoxy-22,23-dihydro-C-076-Bla-aglycone from US-PS 4,173,571.

Compounds in which R represents sec.-butyl shall here and hereinafter also be considered as milbemcyin derivatives although according to conventional classification they are derived from avermectin derivatives. Avermectin-aglycones (with an OH group in the 13-position) can, however, be converted into milbemycin homologues in accordance with US-PS 4 173 571.

The constitution of natural antibiotics S541 is known from DE-OS 35 32 794 and is as follows:

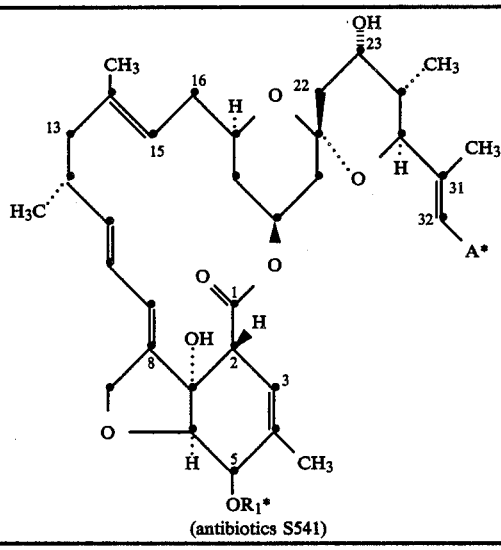

(antibiotics S541)

| Factor A | A* = isoC$_3$H$_7$ | R$_1$* = H |
| Factor B | A* = CH$_3$ | R$_1$* = CH$_3$ |
| Factor C | A* = CH$_3$ | R$_1$* = H |
| Factor D | A* = C$_2$H$_5$ | R$_1$* = H |
| Factor E | A* = C$_2$H$_5$ | R$_1$* = CH$_3$ |
| Factor F | A* = isoC$_3$H$_7$ | R$_1$* = CH$_3$ |

In order to simplify the nomenclature, hereinafter the derivatives of antibiotic S541 are classified according to these factors as derivatives of S541A, S541B, S541C, S541D, S541E and S541F.

Compounds of formula VI in which R$_2$ represents the group

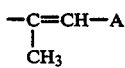

and A has the meaning given for formula VI, which can be used as starting materials in the process according to the invention, can be produced in a manner known per se from the natural antibiotics S541.

The hydroxy group in the 23-position in antibiotics S541 can be removed analogously to the method described in US-PS 4 328 335, and the antibiotics S541 can thus be converted into the corresponding 23-deoxy derivatives. Those compounds having a free 5-OH group (R$_1$*=H) must first be protected selectively by reaction with one of the silylation reagents Y-Si(R$_5$)(R$_6$)(R$_7$) indicated hereinafter or with tert.-butyl-dimethylsilyloxyacetyl chloride. The reaction of those protected compounds in which R$_1$* has been replaced by Si(R$_5$)(R$_6$)(R$_7$) or C(=O)CH$_2$OSi(CH$_3$)$_2$t-C$_4$H$_9$ and the 23-C atom has been substituted by OH, with p-methylphenyl-chlorothionoformate yields derivatives of antibiotics S541 that are substituted at the 23-position by p—CH$_3$—C$_6$H$_4$—O—C(=S)—O. These 23-O-(4-methylphenoxy)thiocarbonyl derivatives of antibiotics S541 are then reduced with tributyltin hydride in toluene in the presence of azobisisobutyronitrile at from 80° C. to 120° C. to form the corresponding 23-deoxy derivatives (position 23 unsubstituted).

Silylation or acylation of the 5-OH group is used to produce all those derivatives of formulae I, II and IV in which R$_1$ has a meaning other than hydrogen (R$_1$=OH-protecting group). For silylation it is advantageous to use a silane of the formula Y-Si(R$_5$)(R$_6$)(R$_7$) in which R$_5$, R$_6$ and R$_7$, preferably independently of one another, represent C$_1$–C$_6$-alkyl, benzyl or phenyl and, together with the silicon atom, form, for example, one of the groups trimethylsilyl, tris(tert.-butyl)silyl, thexyldimethylsilyl, diphenyl-tert.-butylsilyl, bis(isopropyl)methylsilyl, triphenylsilyl and especially tert.-butyldimethylsilyl. Y represents a silyl-leaving group which includes, for example, bromine, chlorine, cyano, azido, acetamido, trifluoroacetoxy and trifluoromethane-sulphonyloxy. This list does not constitute a limitation; the person skilled in the art will know of other typical silyl-leaving groups. The 5-OH group can also be in benzyl ether or methoxymethyl ether form.

The introduction of the acyl group is customarily effected using the corresponding acyl halides or acyl anhydrides and is preferably used to introduce the R$_4$-C(O) group defined at the beginning. Of the acyl halides, the chlorides and bromides are preferred.

5-O-silylations and 5-O-acylations are carried out in an anhydrous medium, preferably in inert solvents and more especially in aprotic solvents. The reaction is advantageously carried out in a temperature range of from 0° C. to +80° C., preferably from +10° to +40° C. Preferably, an organic base is added. Suitable bases are, for example, tertiary amines, such as triethylamine, triethylenediamine, triazole and preferably pyridine, imidazole or 1,8-diazabicyclo[5.4.0]undec-7-ene (DBU).

The removal of these silyl radicals R$_1$ in the 5-position is effected by selective mild hydrolysis (→R$_1$=H) with, for example, arylsulphonic acid in alcoholic solution, HF in acetonitrile, HFx.pyridine in tetrahydrofuran or according to another method known to the person skilled in the art.

All the steps included in the described process for the preparation of compounds of formula I form part of the present invention.

The compounds of formula I are excellently suitable for controlling pests of animals and plants, including ectoparasites of animals. These last-mentioned pests comprise those of the order of Acarina, in particular pests of the families Ixodidae, Dermanyssidae, Sarcoptidae, Psoroptidae; of the orders Mallophaga, Siphonaptera, Anoplura (e.g. family of the Haemotopinidae); and of the order Diptera, in particular pests of the families Muscidae, Calliphoridae, Oestridae, Tabanidae, Hippoboscidae and Gastrophilidae.

The compounds of formula I can also be used to combat hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects that are parasites of plants. When used to control spider mites of the order Acarina, they are effective against eggs, nymphs and adults of Tetranychidae (Tetranychus spp. and Panonychus spp.).

They also have excellent activity against sucking insects of the order Homoptera, in particular against pests of the families Aphididae, Delphacidae, Cicadellidae, Psyllidae, Coccidae, Diaspididae and Eriophydidae (e.g. the rust mite on citrus fruit); of the orders Hemiptera, Heteroptera and Thysanoptera; and against plant-feeding insects of the orders Lepidoptera, Coleoptera, Diptera and Orthoptera.

They are also suitable as soil insecticides against soil pests.

The compounds of formula I are therefore effective against all developmental stages of sucking and feeding insects in crops of useful plants, such as cereals, cotton, rice, maize, soybeans, potatoes, vegetables, fruits, tobacco, hops, citrus fruit, avocados and others.

The compounds of formula I are also effective against plant nematodes of the species Meloidogyne, Heterodera, Pratylenchus, Ditylenchus, Radopholus, Rhizoglyphus and others.

The compounds are also effective against helminths in all developmental stages, and among these the endoparasitic nematodes which can be the cause of severe diseases in mammals and fowl, for example in sheep, pigs, goats, cattle, horses, donkeys, dogs, cats, guinea pigs and cage-birds. Typical nematodes having this indication are: Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides. Certain species of the genera Nematodirus, Cooperia and Oesophagostomum attack the intestinal tract of the host animal, whereas others of the species Haemonchus and *Ostertagia parasiticise* the stomach, and those of the species *Dictyocaulus parasiticise* the lung tissue. Parasites of the families Filariidae and Setariidae are found in the internal cell tissue and organs, e.g. in the heart, blood vessels, lymph vessels and in subcutaneous tissue. In this connection, particular mention is to be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae, which occur in the blood, in tissue and various organs, and, in addition, against Dracunculus and parasites of the species Strongyloides and Trichinella which infest in particular the gastro-intestinal tract.

The compounds of formula I are used in unmodified form, or preferably together with the adjuvants conventionally employed in the art of formulation, and can therefore be formulated in known manner, for example to emulsifiable concentrates, directly sprayable or dilutable solutions, dilute emulsions, wettable powders, soluble powders, dusts, granulates, and also encapsulations in, for example, polymer substances. As with the compositions, the methods of application, such as spraying, atomising, dusting, scattering or pouring, are chosen in accordance with the intended objectives and the prevailing circumstances.

The compounds of formula I are administered to warm-blooded animals in doses of from 0.01 to 10 mg/kg body weight. In the case of enclosed areas they are advantageously applied at rates of from 10 g to 1000 g per hectare. They are also used in stables, pens, stalls or other areas.

The formulations, i.e. the compositions, preparations or mixtures containing the active ingredient of formula I are prepared in known manner, for example by homogeneously mixing and/or grinding the active ingredients with extenders, for example solvents, solid carriers and, in some cases, surface-active compounds (surfactants).

Suitable solvents are: aromatic hydrocarbons, preferably the fractions containing 8 to 12 carbon atoms, for example xylene mixtures or substituted naphthalenes, phthalates such as dibutyl phthalate or dioctyl phthalate, aliphatic hydrocarbons such as cyclohexane or paraffins, alcohols, and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils such as epoxidised coconut oil or soybean oil; or water.

The solid carriers used, for example for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable nonsorbent carriers are materials such as calcite or sand. In addition a great number of granulated materials of inorganic or organic nature can be used, for example especially dolomite or pulverised plant residues.

Depending upon the nature of the active ingredient to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), for example the sodium or potassium salts of oleic or stearic acid, or of natural fatty acid mixtures which can be obtained, for example, from coconut oil or tallow oil. Further suitable surfactants are also the fatty acid methyl taurin salts.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and generally contain a $C_8$–$C_{22}$-alkyl radical which also includes the alkyl moiety of acyl radicals, for example the sodium or calcium salt of lignosulphonic acid, of dodecylsulphate, or of a mixture of fatty alcohol sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde.

Also suitable are corresponding phosphates, for example salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, for example polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulphates or ethylsulphates, for example stearyltrimethylammonium chloride or benzyldi(2-chloroethyl)ethylammonium bromide.

The surfactants customarily employed in the art of formulation are described, inter alia, in the following publication:

"1986 International McCutcheon's Emulsifiers and Detergents", The Manufacturing Confectioner Publishing Co., Glen Rock, N.J., USA.

The pesticidal compositions usually contain 0.01 to 95%, preferably 0.1 to 80%, of active ingredient of formula I, 5 to 99.99% of a solid or liquid adjuvant, and 0 to 25%, preferably 0.1 to 25%, of a surfactant.

Whereas commercial products are preferably formulated as concentrates, the end user will normally employ diluted formulations containing from 1 to 10,000 ppm of active ingredient.

The present invention therefore relates also to pesticidal compositions that contain in addition to customary carriers and/or dispersion agents at least one compound of formula I as active ingredient.

The compositions may also contain further ingredients, such as stabilisers, antifoams, viscosity regulators, binders and tackifiers, as well as fertilisers or other active ingredients in order to obtain special effects.

PREPARATION EXAMPLES

Preparation of Intermediates

A1. Preparation of 5-O-tert.-butyldimethylsilyl-13$\beta$-[2-(1,3-dioxolan-2-yl)-ethyl]-13$\alpha$-hydroxy-milbemycin $A_4$ A solution of 2.40 ml of 2-(2-bromoethyl)-1,3-dioxolan in 10 ml of THF were added within a period of 2½ hours at 40° C. to a suspension of 650 mg of magnesium chips in 20 ml of tetrahydrofuran (THF). In order to initiate the formation of the Grignard reagent, a few crystals of iodine were added at the beginning of the reaction. The reaction mixture was then stirred for a further 30 minutes at 40° C. under an argon atmosphere and then decanted. There was thus obtained a 0.2M solution of 2-(1,3-dioxolan-2-yl)-ethylmagnesium bromide in THF.

A solution of 1.006 g of 5-O-tert.-butyldimethylsilyl-13-oxo-milbemycin $A_4$ in 8 ml of THF was cooled to $-15°$ C. and then 17.0 ml of the 0.2M solution of 2-(1,3-dioxolan-2-yl)-ethylmagnesium bromide in THF were added within a period of 30 minutes. After stirring for 30 minutes at $-15°$ C., 5 ml of saturated $NH_4Cl$ solution were carefully added and then the reaction mixture was poured onto 100 ml of saturated $NaHCO_3$ solution and extracted three times with 150 ml of ether. The organic phases were washed with 100 ml of saturated NaCl solution, dried with $MgSO_4$ and concentrated by evaporation. Chromatography of the crude product on silica gel with hexane/dimethoxyethane 6:1 yielded, in addition to 87 mg (8%) of the C(13)-epimer, 969 mg (84%) of product.

Mass spectrum (MS): m/e: 772 (M+, $C_{43}H_{68}O_{10}Si$).
$^1$H-NMR (300 MHz, $CDCl_3$): 3.05 ppm (dt, $J_d$=2.5, $J_t$=9) ($C_{25}H$), 4.42 ppm (bs, w½=11) ($C_5H$), 4.85 ppm (t, J=3) (OC$\underline{H}$($CH_2$)O).

A2. Preparation of 13$\beta$-[2-(1,3-dioxolan-2-yl)-ethyl]-13$\alpha$-hydroxy-milbemycin $A_4$ A solution of 40 mg of 5-O-tert.-butyldimethylsilyl-13$\beta$-[2-(1,3-dioxolan-2-yl)-ethyl-13$\alpha$-hydroxy-milbemycin $A_4$ in 1 ml of a $HF_x$.pyridine/THF solution (prepared from 6.5 ml of $HF_x$.pyridine, 15.7 ml of pyridine and 50 ml of THF) was stirred at room temperature for 18 hours. The reaction mixture was then poured onto 50 ml of saturated $NaHCO_3$ solution and extracted with 100 ml of diethyl ether. The organic phase was washed with 50 ml of saturated NaCl solution, dried with $MgSO_4$ and concentrated by evaporation. After chromatography of the crude product on silica gel with hexane/ethyl acetate 1:1, 27 mg (79%) of product were obtained.

MS: (m/e): 658 (M+, $C_{37}H_{54}O_{10}$).
$^1$H-NMR (300 MHz, $CDCl_3$): 3.07 ppm (dt, $J_d$=2.5, $J_t$=9) ($C_{25}H$), 4.28 ppm (t, J=7) ($C_5H$), 4.85 ppm (t, J=4) (OC$\underline{H}$($CH_2$)O).

A3. Preparation of 5-O-tert.-butyldimethylsilyl-13$\beta$-[2-(1,3-dioxolan-2-yl)-ethyl]-13$\alpha$-hydroxy-milbemycin $A_3$ In a manner analogous to that described in Example A1 the title compound is obtained from 420 mg of 5-O-tert.-butyldimethylsilyl-13-oxo-milbemycin $A_3$ and 7.0 ml of a 0.2M solution of 2-(1,3-dioxolan-2-yl)-ethylmagnesium bromide.

Mass spectrum (MS): (m/e): 758 (M+, $C_{42}H_{66}O_{10}Si$).

A4. Preparation of 13β-[2-(1,3-dioxolan-2-yl)-ethyl]-13α-hydroxy-milbemycin A₃

The title compound can be prepared analogously to Example A2 from 5-O-tert.-butyldimethylsilyl-13β-[2-(1,3-dioxolan-2-yl)-ethyl]-13α-hydroxy-milbemycin A₃.
Mass spectrum (MS): (m/e): 644 (M+, $C_{36}H_{52}O_{10}$).

PREPARATION OF COMPOUNDS OF FORMULA I

H1. Preparation of milbemycin A₄-13-spiro-2'-[5'-methoxytetrahydrofuran]

A solution of 50 mg of 5-O-tert.-butyldimethylsilyl-13β-[2-(1,3-dioxolan-2-yl)-ethyl]-13α-hydroxy-milbemycin A₄ in 1 ml of a 1% solution of p-toluenesulphonic acid in methanol was stirred for 90 minutes at room temperature. The reaction mixture was then poured onto 50 ml of saturated NaHCO₃ solution and extracted with 100 ml of diethyl ether. The organic phase was washed with 50 ml of saturated NaCl solution, dried with MgSO₄ and concentrated by evaporation. After chromatography of the crude product on silica gel with hexane/ethyl acetate 2:1, it was possible to isolate 35 mg (86%) of product in the form of a mixture of epimers at C5' (isomer A:isomer B approximately 3:1).

MS: (m/e): 628 (M+, $C_{36}H_{52}O_9$).

$^1$H-NMR (300 MHz, CDCl₃): 3.09 ppm (dt, $J_d=2.5$, $J_t=9$) (C₂₅H), 3.40* and 3.45 ppm (2s) (CH₃O), 4.03 and 4.12* ppm (2s) (OH), 4.29 ppm (6s, w½=15) (C₅H), 4.99* ppm (d, J=4) and 5.10 ppm, (dd, J=4, J'=2) (OC$\underline{H}$(CH₂)O).

H2. Preparation of 5-O-tert.-butyldimethylsilyl-milbemycin A₄-13-spiro-2'-[5'-(2''-ethoxyethoxy)-tetrahydrofuran]

24 mg of (±)-camphor-10-sulphonic acid were added to a solution of 80 mg of 5-O-tert.-butyldimethylsilyl-13β-[2-(1,3-dioxolan-2-yl)-ethyl]-13β-hydroxy-milbemycin A₄ and 200 μl of ethylene glycol monoethyl ether in 2 ml of methylene chloride. After stirring for 2 hours at room temperature, the reaction mixture was poured onto 50 ml of saturated NaHCO₃ solution and extracted with 100 ml of diethyl ether. The organic phase was washed with 50 ml of saturated NaCl solution, dried with MgSO₄ and concentrated by evaporation. Chromatography of the crude product on silica gel with hexane/ethyl acetate 6:1 yielded 62 mg (50%) of isomer A product and 32 mg (26%) of isomer B product.

Isomer A:
MS: (m/e): 800 (M+, $C_{45}H_{72}O_{10}Si$).

$^1$H-NMR (300 MHz, CDCl₃): 3.08 ppm (dt, $J_d=2.5$, $J_t=9$) (C₂₅H), 4.09 ppm (s) (OH), 4.42 ppm (bs, w½=10) (C₅H), 5.13 ppm (bs, w½=6) (OC$\underline{H}$(CH₂)O).

Isomer B:
MS: (m/e): 800 (M+, $C_{45}H_{72}O_{10}Si$).

$^1$H-NMR (300 MHz, CDCl₃): 3.07 ppm (dt, $J_d=2.5$, Jt=9) (C₂₅H), 4.03 ppm (s) (OH), 4.42 ppm (bs, w½=10) (C₅H), 5.23 ppm (bd, J=3) (OC$\underline{H}$(CH₂)O), 5.51 ppm (dd, J=11, J'=6) (C₁₅H).

H3. Preparation of milbemycin A₄-13-spiro-2'-[5'-(2'''-ethoxyethoxy)tetrahydrofuran]

(a) Isomer A
A solution of 58 mg of 5-O-tert.-butyldimethylsilyl-13-spiro-2'-[5'-(2'''-ethoxyethoxy)-tetrahydrofuran] (isomer A) in 1 ml of HF$_x$·pyridine/THF solution (see above) was stirred for 16 hours at room temperature. The reaction mixture was then poured onto 50 ml of saturated NaHCO₃ solution and extracted with 100 ml of diethyl ether. The organic phase was washed with 50 ml of saturated NaCl solution, dried with MgSO₄ and concentrated by evaporation. Chromatography of the crude product on silica gel with hexane/ethyl acetate 2:1 yielded 47 mg (94%) of product.

MS: (m/e): 686 (M+, $C_{39}H_{58}O_{10}$).

$^1$H-NMR (300 MHz, CDCl₃): 3.08 ppm (dt, $J_d=2.5$, $J_t=9$) (C₂₅H), 4.10 ppm (s) (OH), 4.28 ppm (t, J=7) (C₅H), 5.13 ppm (bd, J=4) (OC$\underline{H}$(CH₂)O).

(b) Isomer B
22 mg (88%) of product were obtained from 29.5 mg of 5-O-tert.-butyldimethylsilyl-13-spiro-2'-[5'-(2''-ethoxyethoxy)-tetrahydrofuran] (isomer B) analogously to procedure H3.a.

MS: (m/e): 686 (M+, $C_{39}H_{58}O_{10}$).

$^1$H-NMR (300 MHz, CDCl₃): 3.06 ppm (dt, $J_d=2.5$, $J_t=9$) (C₂₅H), 4.03 ppm (s) (OH), 4.28 ppm (t, J32 7) (C₅H), 5.22 ppm (bd, J=4) (OC$\underline{H}$(CH₂)O), 5.50 ppm (dd, J=11, J'=5) (C₁₅H).

H4. Preparation of 5-O-tert.-butyldimethylsilylmilbemycin A₄-13-spiro-2'-[5'-(2'',2''-dimethylpropoxy)-tetrahydrofuran]

36 mg of (±)-camphor-10sulphonic acid were added to a solution of 120 mg of 5-O-tert.-butyldimethylsilyl-13β-[2-(1,3-dioxolan-2-yl)-ethyl]-13α-hydroxy-milbemycin A₄ and 274 mg of neopentyl alcohol in 2 ml of methylene chloride. After stirring for 2 hours at room temperature, the reaction mixture was worked up as described under Preparation Example H2. After chromatography of the crude product on silica gel with hexane/diethyl ether 5:1, it was possible to isolate 64 mg (52%) of isomer A product and 35 mg (28%) of isomer B product.

Isomer A:
MS: (m/e): 798 (M+, $C_{46}H_{74}O_9Si$).

$^1$H-NMR (300 MHz, CDCl₃): 0.88 ppm (s) (C(CH₃)₃), 2.96 ppm (d, J=9) (OCHHC(CH₃)₃), 3.08 ppm (dt, $J_d=2.5$, $J_t=9$) (C₂₅H), 3.50 ppm (d, J=9) (OCHHC(CH₃)₃), 4.09 ppm (s) (OH), 4.42 ppm (bs, w½=10) (C₅H), 4.07 ppm (bd, J=3) (OC$\underline{H}$(CH₂)O).

Isomer B:
MS: (m/e): 798 (M+, $C_{46}H_{74}O_9Si$).

$^1$H-NMR (300 MHz, CDCl₃): 0.88 ppm (s) (C(CH₃)₃), 3.02 ppm (dt, $J_d=2.5$, $J_t=9$) (C₂₅H), 3.06 ppm (d, J=9) (OCHHC(CH₃)₃), 3.51 ppm (d, J=9) (OCHHC(CH₃)₃), 4.11 ppm (s) (OH), 4.42 ppm (bs, w½=10) (C₅H), 5.14 ppm (dd, J=5, J'=2.5) (OC$\underline{H}$(CH₂)O), 5.56 ppm (t, J=7.5) (C₁₅H).

H5. Preparation of milbemycin A₄-13-spiro-2'-[5'-(2'',2''-dimethylpropoxy)tetrahydrofuran]

(a) Isomer A
47 mg (90%) of product were obtained from 61 mg of 5-O-tert.-butyldimethylsilyl-milbemycin A₄-13-spiro-2'-[5'-(2'',2''-dimethylpropoxy)-tetrahydrofuran] (isomer A) analogously to Preparation Example H3.

MS: (m/e): 684 (M+, $C_{40}H_{60}O_9$).

$^1$H-NMR (300 MHz, CDCl₃): 0.87 ppm (s) (C(CH₃)₃), 2.95 ppm (d, J=9) (OCHHC(CH₃)₃), 3.07 ppm (dt, $J_d=2.5$, $J_t=9$) (C₂₅H), 3.40 ppm (d, J=9)

(OCHHC(CH$_3$)$_3$), 4.11 ppm (s) (OH), 4.28 ppm (t, J=7) (C$_5$H), 5.06 ppm (bs, w½=6) (OCH(CH$_2$)O).

(b) Isomer B 22 mg (85%) of product were obtained from 29 mg of 5-O-tert.-butyldimethylsilyl-milbemycin A$_4$-13-spiro-2'-[5'-(2",2"-dimethylpropoxy)-tetrahydrofuran] (isomer B) analogously to Preparation Example H3.

MS: (m/e): 684 (M$^+$, C$_{40}$H$_{60}$O$_9$).

$^1$H-NMR (300 MHz, CDCl$_3$): 0.88 ppm (s) (C(CH$_3$)$_3$), 3.01 ppm (dt, J$_d$=2.5, J$_t$=9) (C$_{25}$H), 3.05 ppm (d, J=9) (OCHHC(CH$_3$)$_3$), 3.50 ppm (d, J=9) (OCHHC(CH$_3$)$_3$), 4.09 ppm (s) (OH), 4.28 ppm (t, J=7) (C$_5$H), 5.15 ppm (dd, J=5, m J'=2.5) (OCH(CH$_2$)O), 5.55 ppm (t, J=8) (C$_{15}$H).

H6. Preparation of 5-O-tert.-butyldimethylsilyl-milbemycin A$_4$-13-spiro-2'-[5'-(2"-(2'''-(2''''-hydroxyethoxy)-ethoxy)-ethoxy)-tetrahydrofuran]

36 mg of (±)-camphor-10-sulphonic acid were added to a solution of 120 mg of 5-O-tert.-butyldimethylsilyl-13β-[2-(1,3-dioxolan-2-yl)-ethyl]-13α-hydroxy-milbemycin A$_4$ and 828 μl of triethylene glycol in 2 ml of methylene chloride. After stirring for 2 hours at room temperature, the reaction mixture was worked up as described under Preparation Example H2. Chromatography of the crude product on silica gel with hexane/ethyl acetate 1:1 yielded 96 mg (72%) of product in the form of a mixture of epimers at C5' (isomer A:isomer B approximately 3:1).

MS: (m/e): 860 (M$^+$, C$_{47}$H$_{76}$O$_{12}$Si).

$^1$H-NMR (300 MHz, CDCl$_3$): 3.08 ppm (dt, J$_d$=2.5, J$_t$=9) (C$_{25}$H), 4.02 ppm and 4.10* ppm (2s) (OH), 4.42 ppm (bs, w½=10) (C$_5$H), 5.12* ppm (bs, w½=6) and 5.16 ppm, (dd, J=5, J'=2) (OCH(CH$_2$)O).

H7. Preparation of milbemycin A$_4$-13-spiro-2'-[5'-(2"-(2'''-(2''''-hydroxy-ethoxy)-ethoxy)-ethoxy)-tetrahydrofuran]

39 mg (90%) of product, in the form of a mixture of epimers at C5' (isomer A:isomer B approximately 2.5:1), were obtained from 50 mg of 5-O-tert.-butyldimethylsilyl-milbemycin A$_4$-13-spiro-2'-[5'-(2"-(2'''-(2''''-hydroxyethoxy)-ethoxy)-ethoxy)-tetrahydrofuran] analogously to Preparation Example H3.

MS: (m/e): 746 (M$^+$, C$_{41}$H$_{62}$O$_{12}$).

$^1$H-NMR (300 MHz, CDCl$_3$): 3.07 ppm (bt, J=9) (C$_{25}$H), 4.00 ppm and 4.10* ppm (2s) (OH), 4.27 ppm (t, J=7) (C$_5$H), 5.11* ppm (bt, J=2) and 5.22 ppm, (dd, J=5, J'=2) (OCH(CH$_2$)O).

H8. Preparation of 5-O-tert.-butyldimethylsilyl-milbemycin A$_4$-13-spiro-2'-[5'-(2"-(2'''-(2''''-(chloroacetoxy)-ethoxy)-ethoxy)-ethoxy)-tetrahydrofuran]

At 0° C., 1 μl of chloroacetyl chloride was added to a solution of 42 mg of 5-O-tert.-butyldimethylsilyl-milbemycin A$_4$-13-spiro-2'-[5'-(2"-(2'''-(2''''-hydroxyethoxy)-ethoxy)-ethoxy)-tetrahydrofuran] [mixture of epimers at C5' (isomer A:isomer B approximately 3:1)] and 39 μl of pyridine in 2 ml of methylene chloride. After stirring for 6 hours at 0° C., the reaction mixture was poured onto 50 ml of 1N HCl solution and extracted with 100 ml of diethyl ether. The organic phase was washed with 50 ml of saturated NaHCO$_3$ solution and 50 ml of saturated NaCl solution, dried with MgSO$_4$ and concentrated. Chromatography of the crude product on silica gel with hexane/ethyl acetate 3:1 yielded 42 mg (92%) of product in the form of a mixture of epimers at C5' (isomer A:isomer B approximately 3:1).

MS: (m/e): 936 (M$^+$, C$_{49}$H$_{77}$ClO$_{13}$Si).

$^1$H-NMR (300 MHz, CDCl$_3$): 3.07 ppm (dt, J$_d$=2.5, J$_t$=9) (C$_{25}$H), 4.00 ppm and 4.08* ppm (2s) (OH), 4.08 ppm (s) (CH$_2$Cl), 4.41 ppm (bs, w½=10) (C$_5$H), 5.10* ppm (bt, J=3) and 5.22 ppm, (dd, J=5, J'=2.5) (OCH(CH$_2$)O).

H9. Preparation of milbemycin A$_4$-13-spiro-2'-[5'-(2"-(2'''-(2''''-(chloroacetoxy)-ethoxy)-ethoxy)-ethoxy)-tetrahydrofuran]

26 mg (75%) of product, in the form of a mixture of epimers at C5' (isomer A:isomer B approximately 3:1), were obtained from 39 mg of 5-O-tert.-butyldimethylsilyl-milbemycin A$_4$-13-spiro-2'-[5'-(2"-(2'''-(2''''-(chloroacetoxy)-ethoxy)-ethoxy)-ethoxy)-tetrahydrofuran] [mixture of epimers at C5' (isomer A:isomer B approximately 3:1)] analogously to Preparation Example H3.

MS: (m/e): 822 (M+, C$_{43}$H$_{62}$ClO$_{13}$).

1H-NMR (300 MHz, CDCl$_3$): 3.07 ppm (dt, J$_d$=2.5, J$^t$=9) (C$_{25}$H), 4.00 ppm and 4.10* ppm (2s) (OH), 4.08 ppm (s) (CH$_2$Cl), 4.27 ppm (t, J=7) (C$_5$H), 5.11* ppm (bt, J=2.5) and 5.22 ppm (m) (OCH(CH$_2$)O).

In accordance with the process described above it is also possible to prepare, for example, the following compounds of formula I:

H10. 5-O-tert.-butyldimethylsilyl-milbemycin A$_4$-13-spiro-2'-[5'-benzyloxytetrahydrofuran]

(a) Isomer A:

MS: (m/e): 818 (M$^+$, C$_{48}$H$_{70}$O$_9$Si).

$^1$H-NMR: (300 MHz, CDCl3): 3.07 ppm (dt, J$_d$=2.5, J$_t$=9) (C$_{25}$H), 4.09 ppm (s) (OH), 4.42 ppm (bs, w½=11) (C$_5$H), 4.48 ppm (d, J=11.5) (OCHC$_6$H$_5$), 4.82 ppm (d, J=11.5) (OCHHC$_6$H$_5$), 5.20 ppm (bt, J=2.5) (OCH(CH$_2$)O), 7.33 ppm (m) (C$_6$H$_5$).

(b) Isomer B:

MS: (m/e): 818 (M$^+$, C$_{48}$H$_{70}$O$_9$Si).

$^1$H-NMR (300 MHz, CDCl$_3$): 3.00 ppm (dt, J$_d$=2.5, J$_t$=9) (C$_{25}$H), 4.12 ppm (s) (OH), 4.41 ppm (bs, w½=10) (C$_5$H), 4.57 ppm (d, J=11.5) (OCHHC$_6$H$_5$), 4.86 ppm (d, J=11.5) (OCHHC$_6$H$_5$), 5.54 ppm (dd, J=10, J'=5) (C$_{15}$H), 7.32 ppm (m) (C$_6$H$_5$).

H11.: Milbemycin A$_4$-13-spiro-2'-[5-benzyloxytetrahydro-furan]

(a) Isomer A:

MS: (m/e): 704 (M$^+$, C$_{42}$H$_{56}$O$_9$).

$^1$H-NMR (300 MHz, CDCl$_3$): 3.07 ppm (dt, J$_d$=2.5, J$_t$=9) (C$_{25}$H), 4.10 ppm (s) (OH), 4.28 ppm (t, J=7) (C$_5$H), 4.48 ppm (d, J=11.5) (OCHHC$_6$H$_5$), 4.82 ppm (d, J=11.5) (OCHHC$_6$H$_5$), 5.20 ppm (bt, J=2.5) (OCH(CH$_2$)O), 7.33 ppm (m) (C$_6$H$_5$).

(b) Isomer B:

MS: (m/e): 704 (M$^+$, C$_{42}$H$_{56}$O$_9$).

$^1$H-NMR (300 MHz, CDCl$_3$): 3.00 ppm (dt, J$_d$=2.5, J$_t$=9) (C$_{25}$H), 4.10 ppm (s) (OH), 4.27 ppm (t, J=7) (C$_5$H), 4.57 pp, (d, J=11.5) (OCHHC$_6$H$_5$), 4.85 ppm (d, J=11.5) (OCHHC$_6$H$_5$), 5.30 ppm (bt, J=2.5) (OCH(CH$_2$)O), 7.31 ppm (m) (C$_6$H$_5$).

H12: 5-O-tert.-butyldimethylsilyl-milbemycin A$_4$-13-spiro-2'-[5'-cyclohexyloxytetrahydrofuran]

(a) Isomer A:

MS: (m/e): 810 (M$^+$, C$_{47}$H$_{74}$O$_9$Si).

$^1$H-NMR (300 MHz, CDCl$_3$): 3.07 ppm (dt, J$_d$=2.5, J$_t$=9) (C$_{25}$H), 3.60 ppm (m) (OCH(CH$_2$)CH$_2$), 4.09 ppm (s) (OH), 4.41 ppm (bs, w½=10) (C$_5$H).

(b) Isomer B:

MS: (m/e): 810 (M+, C$_{47}$H$_{74}$O$_9$Si).

$^1$H-NMR (300 MHz, CDCl$_3$): 3.01 ppm (dt, J$_d$=2.5, J$_t$=9) (C$_{25}$H), 3.62 ppm (m) (OCH(CH$_2$)CH$_2$), 4.08 ppm (s) (OH), 4.40 ppm (bs, w½=10) (C$_5$H), 5.55 ppm (bs, J=8) (C$_{15}$H).

H13: Milbemycin A$_4$-13-spiro-2'-[5'-cyclohexyloxytetra-hydrofuran]

(a) Isomer A:

MS: (m/e): 696 (M+, C$_{41}$H$_{60}$O$_9$).

$^1$H-NMR (300 MHz, CDCl$_3$): 3.08 ppm (dt, J$_d$=2.5, J$_t$=9) (C$_{25}$H), 3.62 ppm (m) (OCH(CH$_2$)CH$_2$), 4.10 ppm (s) (OH), 4.28 ppm (t, J=7) (C$_5$H).

(b) Isomer B:

MS: (m/e): 696 (M+, C$_{41}$H$_{60}$O$_9$).

$^1$H-NMR (300 MHz, CDCl$_3$): 3.02 ppm (dt, J$_d$=2.5, J$_t$=9) (C$_{25}$H), 3.62 ppm (m) (OCH(CH$_2$)CH$_2$), 4.07 ppm (s) (OH), 4.27 ppm (t, J=7) (C$_5$H), 5.56 ppm (dd, J=10, J'=5) (C$_{15}$H).

H14: 5-O-tert.-butyldimethylsilyl-milbemycin A$_4$-13-spiro-2'-[5'-(2''-(2'''-methoxy-ethoxy)-ethoxy)-tetrahydro-furan]

Mixture of epimers at C5' (isomer A:isomer B approx. 3:1).

MS: (m/e): 830 (M+, C$_{46}$H$_{74}$O$_{11}$Si).

1H-NMR (300 MHz, CDCl$_3$): 3.08 ppm (bt, J=9) (C$_{25}$H), 3.36 ppm (s) (CH$_3$O), 4.02 and 4.09* ppm (2s) (OH), 4.41 ppm (bs, w½=11) (C$_5$H), 5.12* ppm (bs, w½=6) and 5.23 ppm (bs, w½=6) (OCH(CH$_2$)O).

H15: Milbemycin A$_{14}$-13-spiro-2'-[5'-(2''-(2'''-methoxy-ethoxy)-ethoxy)-tetrahydrofuran]

Mixture of epimers at C5' (isomer A:isomer B approx. 2:3)

MS: (m/e): 716 (M+, C$_{40}$H$_{60}$O$_{11}$).

1H-NMR (300 MHz, CDCl$_3$): 3.08 ppm (dt, J$_d$=2.5, J$_t$=9) (C$_{25}$H), 3.38 ppm (s) (CH$_3$O), 4.01* and 4.10 ppm (2s) (OH), 4.29 ppm (t, J=7) (C$_5$H), 5.12 pp, (bs, w½=7) and 4.23* ppm (bs, w½=6) (OCH(CH$_2$)O).

H16: 5-O-tert.-butyldimethylsilyl-milbemycin A$_4$-13-spiro-2'-[5'-((3''-methyl-oxetan-3''-yl)-methoxy)-tetrahydrofuran]

Mixture of epimers at C5' (isomer A:isomer B approx. 1:1)

MS: (m/e): 812 (M+, C$_{46}$H$_{72}$O$_{10}$Si).

$^1$H-NMR (300 MHz, CDCl$_3$): 3.02 and 3.07 ppm (2dt, J$_d$=2.5, J$_t$=9) (C$_{25}$H), 3.40 and 3.47 ppm (2d, J=10) (OCHHC), 3.87 and 3.88 ppm (2d, J=10) (OCHHC), 4.09 and 4.10 ppm (2s) (OH), 5.12 ppm (bd, J=3.5) and 5.20 ppm, (dd, J=4.5, J'=2) (OCH(CH$_2$)O).

H17: Milbemycin A$_4$-13-spiro-2'-[5'-((3''-methyloxetan-3''-yl)-methoxy)-tetrahydrofuran]

Mixture of epimers at C5' (isomer A:isomer B approx. 1:1).

MS: (m/e): 698 (M+, C$_{40}$H$_{58}$O$_{10}$).

1H-NMR (300 MHz, CDCl$_3$): 3.02 and 3.07 ppm (2d, J$_d$=2.5, J$_t$=9) (C$_{25}$H), 3.40 and 3.46 ppm (2d, J=10) (OCHHC), 3.86 and 3.88 ppm (2d, J=10) (OCHHC), 4.09 and 4.10 ppm (2s) (OH), 4.28 ppm (t, J=7) (C$_5$H), 5.12 ppm (bd, J=3.5) and 5.20 ppm, (dd, J=5, J'=2) (OCH(CH$_2$)O).

H18: 5-tert.-butyldimethylsilyl-milbemycin A$_4$-13-spiro-2'-[5'-(2''-hydroxyethoxy)-tetrahydrofuran]

Mixtures of epimers at C5' (isomer A:isomer B approx. 1:1).

MS: (m/e): 772 (M+, C$_{43}$H$_{68}$O$_{10}$Si).

1H-NMR (300 MHz, CDCl$_3$): 3.07 ppm (dt, J$_d$=2.5, J$_t$=9) (C$_{25}$H), 3.98 and 4.06* ppm (2s) (OH), 4.41 ppm (bs, w½=11) (C$_5$H), 5.13* ppm (d, J=4.5) and 5.22 ppm, (dd, J=5, J'=2) (OCH(CH$_2$)O).

H19: Milbemycin A$_4$-13-spiro-2'-[5'-(2''-hydroxyethoxy)-tetrahydrofuran]

(a) Isomer A:

MS: (m/e): 658 (M+, C$_{37}$H$_{54}$O$_{10}$).

1H-NMR (300 MHz, CDCl$_3$): 3.07 ppm (dt, J$_d$=2.5, J$_t$=9) (C$_{25}$H), 4.06 ppm (s) (OH), 4.27 ppm (t, J=7) (C$_5$H), 5.13 ppm (d, J=4.5) (OCH(CH$_2$)O).

(b) Isomer B:

MS: (m/e): 658 (M+, C$_{37}$H$_{54}$O$_{10}$).

1H-NMR (300 MHz, CDCl$_3$): 3.07 ppm (dt, J$_d$=2.5, J$_t$=9) (C$_{25}$H), 3.98 ppm (s) (OH), 4.27 ppm (t, J=7) (C$_5$H), 5.22 ppm (dd, J=5, J'=3) (OCH(CH$_2$)O), 5.53 ppm (dd, J=10.5, J'=4.5) (C$_{15}$H).

H20. Preparation of 5-oximino-milbemycin A$_4$-13-spiro-2'-[5'-(2'',2''-dimethoxypropoxy)-tetrahydrofuram]

(a) A solution of 50 mg of milbemycin A$_4$-13-spiro-2'-[5'-(2'',2''-dimethoxypropoxy)-tetrahydrofuran] in 3 ml of dichloromethane is stirred with 95 mg of manganese dioxide for 5 hours at room temperature. The manganese dioxide is filtered off over kieselguhr, and after concentration of the solution, 47 mg of crude 5-oxo-milbemycin A$_{14}$-13-spiro-2'-[5'-(2'',2''-dimethylpropoxy)-tetrahydrofuran] are obtained.

MS: (m/e): 682 (M+, C$_{40}$H$_{58}$O$_9$).

(b) This crude product is dissolved together with 47 mg of hydroxylamine hydrochloride in 1.0 ml of pyridine. After stirring for 1 hour at room temperature, the mixture is worked up with diethyl ether and 1N HCl. Chromatography of the crude product on silica gel with ethyl acetate/hexane 1:3 yields 35 mg of the title compound.

MS: (m/e): 697 (M+, C$_{40}$H$_{59}$NO$_9$).

$^1$H-NMR (300 MHz, CDCl$_3$): 0.88 ppm (s) (C(CH$_3$)$_3$), 2.96 ppm (d, J=9.5) (OCHHC(CH$_3$)$_3$), 3.08 ppm (dt, J$_d$=2.5, J$_t$=9.5) (C$_{25}$H), 3.48 ppm (d, J=9.5) (OCHHC(CH$_3$)$_3$), 4.64 ppm (s) (C6H), 7.62 ppm (s) (N—OH).

H21. Preparation of 5-oximino-milbemycin A$_{14}$-13-spiro-2'-[5'-cyclohexyloxytetrahydrofuran]

(a) 56 mg of manganese dioxide are added to a solution of 30 mg of milbemycin A$_4$-13-spiro-2'-[5'-cyclohexyloxy-tetrahydrofuran] in 3 ml of dichloromethane. After stirring for 2 hours at room temperature, the reaction mixture is filtered over kieselguhr. After concentration of the solution 30 mg of crude 5-oxo-milbemycin A$_4$-13-spiro-2'-[5-cyclohexyloxy-tetrahydrofuran] are obtained.

MS: (m/e): 694 (M+, C$_{41}$H$_{58}$O$_9$).

(b) 29 mg of this crude product and 30 mg of hydroxylamine hydrochloride in 1.0 ml of pyridine are stirred for 2 hours at room temperature. The reaction mixture is worked up with diethyl ether and 1N HCl and after chromatography of the crude product on silica gel with ethyl acetate/hexane 1:3, 23 mg of the title compound are obtained.

MS: (m/e): 709 (M$^+$, $C_{41}H_{59}NO_9$).

$^1$H-NMR (300 MHz, CDCl$_3$): 3.09 ppm (dt, $J_d$=2.5, $J_t$=9.5) (C$_{25}$H), 3.62 ppm (m) (OCH(CH$_2$)CH$_2$), 4.55 ppm (s) (C$_6$H), 7.65 ppm (s) (N—O$\overline{\text{H}}$).

H22. Preparation of 5-oximino-milbemycin A$_4$-13-spiro-2'-[5'-(2''-methylbutoxy)-tetrahydrofuran]

(a) 57 mg of manganese dioxide are added to a solution of 30 mg of milbemycin A$_4$-13-spiro-2'-[5'-(2''-methylbutoxy)-tetrahydrofuran] in 3 ml of dichloromethane. After stirring for 2 hours at room temperature, the reaction mixture is filtered over kieselguhr and, after concentration of the solution, 27 mg of crude 5-oxo-milbemycin A$_4$-13-spiro-2'-[5'-(2''-methylbutoxy)-tetrahydrofuran] are obtained.

MS: (m/e): 682 (M$^+$, $C_{40}H_{58}O_9$).

(b) 26 mg of this crude product are dissolved together with 26 mg of hydroxylamine hydrochloride in 1.0 ml of pyridine. After stirring for 90 minutes at room temperature, the mixture is worked up with diethyl ether and 1N HCl. Chromatography of the crude product on silica gel with ethyl acetate/hexane 1:3 yields 21 mg of the title compound.

MS: (m/e): 697 (M$^+$, $C_{40}H_{59}NO_9$).

$^1$H-NMR (300 MHz, CDCl$_3$): 3.10 ppm (dd, $J_1$=6, $J_2$=9.5) (OC$\overline{\text{H}}$HCH(CH$_3$)C$_2$H$_5$), 3.66 ppm (dd, $J_1$=6, $J_2$=9.5) (OCH$\overline{\text{H}}$CH(CH$_3$)C$_2$H$_5$), 4.64 ppm (s) (C$_6$H), 7.68 ppm (s) (N—O$\overline{\text{H}}$).

H23. Preparation of 5-oximino-milbemycin A$_3$-13-spiro-2'-[5'-(2''-ethoxyethoxy)-tetrahydrofuran]

(a) 60 mg of manganese dioxide are added to a solution of 14.5 mg of milbemycin A$_3$-13-spiro-2'-[5'-(2''-ethoxyethoxy)-tetrahydrofuran] in 3 ml of dichloromethane. After stirring for 90 minutes at room temperature the reaction mixture is filtered over kieselguhr and, after concentration of the solution, 14 mg of crude 5-oxo-milbemycin A3-13-spiro-2'-[5'-(2''-ethoxyethoxy)-tetrahydrofuran] are obtained.

MS: (m/e): 670 (M$^+$, $C_{38}H_{54}O_{10}$).

(b) This crude product is dissolved together with 20 mg of hydroxylamine hydrochloride in 1.0 ml of pyridine. After stirring for one hour at room temperature, the mixture is worked up with diethyl ether and 1N HCl. Chromatography of the crude product on silica gel with ethyl acetate/hexane 1:3 yields 10 mg of the title compound.

MS: (m/e): 685 (M$^+$, $C_{38}H_{55}NO_{10}$).

It is also possible to prepare the following compounds analogously to the procedures described above:

TABLE 1

Compounds of formula I
in which X = —CH(OR$_1$)—, R$_1$ = H and R$_2$ = CH$_3$

| Comp. No. | R$_3$ | Epimer | Physic. constant or Preparation Example |
|---|---|---|---|
| 1.1 | CH$_3$ | A | |
| 1.2 | CH$_3$ | B | |
| 1.3 | CH$_3$ | A/B | m/e: 614 (M$^+$, $C_{35}H_{50}O_9$) |
| 1.4 | C$_2$H$_5$ | A | |
| 1.5 | C$_2$H$_5$ | B | |
| 1.6 | C$_2$H$_5$ | A/B | |
| 1.7 | C$_3$H$_7$—n | A | |
| 1.8 | C$_3$H$_7$—n | B | |
| 1.9 | C$_3$H$_7$—n | A/B | |
| 1.10 | C$_3$H$_7$—i | A | |
| 1.11 | C$_3$H$_7$—i | B | |
| 1.12 | C$_3$H$_7$—i | A/B | |
| 1.13 | C$_4$H$_9$—n | A | |
| 1.14 | C$_4$H$_9$—n | B | |
| 1.15 | C$_4$H$_9$—n | A/B | |
| 1.16 | C$_6$H$_{13}$—n | A/B | |
| 1.17 | C$_{10}$H$_{21}$—n | A/B | |
| 1.18 | CH$_2$OCH$_3$ | A | |
| 1.19 | CH$_2$OCH$_3$ | B | |
| 1.20 | CH$_2$OCH$_3$ | A/B | |
| 1.21 | CH$_2$CH$_2$OH | A | |
| 1.22 | CH$_2$CH$_2$OH | B | |
| 1.23 | CH$_2$CH$_2$OH | A/B | |
| 1.24 | CH$_2$C(CH$_3$)$_3$ | A | m/e: 670 (M$^+$, $C_{39}H_{58}O_9$) |
| 1.25 | CH$_2$C(CH$_3$)$_3$ | B | m/e: 670 (M$^+$, $C_{39}H_{58}O_9$) |
| 1.26 | CH$_2$C(CH$_3$)$_3$ | A/B | |
| 1.27 | Phenyl | A | |
| 1.28 | Phenyl | B | |
| 1.29 | Phenyl | A/B | |
| 1.30 | Benzyl | A | |
| 1.31 | Benzyl | B | |
| 1.32 | Benzyl | A/B | |
| 1.33 | CH$_2$CH$_2$OCH$_3$ | A | |
| 1.34 | CH$_2$CH$_2$OCH$_3$ | B | |
| 1.35 | CH$_2$CH$_2$OCH$_3$ | A/B | |
| 1.36 | CH$_2$CH$_2$OC$_2$H$_5$ | A | m/e: 672 (M$^+$, $C_{38}H_{56}O_{10}$) |
| 1.37 | CH$_2$CH$_2$OC$_2$H$_5$ | B | m/e: 672 (M$^+$, $C_{38}H_{56}O_{10}$) |
| 1.38 | CH$_2$CH$_2$OC$_2$H$_5$ | A/B | |
| 1.39 | CH$_2$CH$_2$OCH$_2$CH$_2$OCH$_3$ | A | |

TABLE 1-continued

Compounds of formula I
in which X = —CH(OR$_1$)—, R$_1$ = H and R$_2$ = CH$_3$

| Comp. No. | R$_3$ | Epimer | Physic. constant or Preparation Example |
|---|---|---|---|
| 1.40 | CH$_2$CH$_2$OCH$_2$CH$_2$OCH$_3$ | B | |
| 1.41 | CH$_2$CH$_2$OCH$_2$CH$_2$OCH$_3$ | A/B | |
| 1.42 | CH$_2$CH$_2$(OCH$_2$CH$_2$)$_2$OH | A | |
| 1.43 | CH$_2$CH$_2$(OCH$_2$CH$_2$)$_2$OH | B | |
| 1.44 | CH$_2$CH$_2$(OCH$_2$CH$_2$)$_2$OH | A/B | |
| 1.45 | CH$_2$CH$_2$(OCH$_2$CH$_2$)$_2$OCOCH$_2$Cl | A | |
| 1.46 | CH$_2$CH$_2$(OCH$_2$CH$_2$)$_2$OCOCH$_2$Cl | B | |
| 1.47 | CH$_2$CH$_2$(OCH$_2$CH$_2$)$_2$OCOCH$_2$Cl | A/B | |
| 1.48 | Cyclohexyl | A | m/e: 682 (M$^+$, C$_{40}$H$_{58}$O$_9$) |
| 1.49 | Cyclohexyl | B | m/e: 682 (M$^+$, C$_{40}$H$_{58}$O$_9$) |
| 1.50 | Cyclohexyl | A/B | |
| 1.51 | 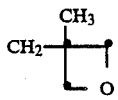 | A | |
| 1.52 | 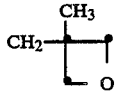 | B | |
| 1.53 | 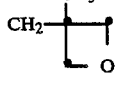 | A/B | |
| 1.54 | CH$_2$Cl$_3$ | A | |
| 1.55 | CH$_2$Cl$_3$ | B | |
| 1.56 | CH$_2$Cl$_3$ | A/B | |
| 1.57 | CH$_2$C(CH$_3$)(CH$_2$Cl)$_2$ | A | |
| 1.58 | CH$_2$C(CH$_3$)(CH$_2$Cl)$_2$ | B | |
| 1.59 | CH$_2$C(CH$_3$)(CH$_2$Cl)$_2$ | A/B | |
| 1.60 | CH$_2$CBr$_3$ | A | |
| 1.61 | CH$_2$CBr$_3$ | B | |
| 1.62 | CH$_2$CBr$_3$ | A/B | |
| 1.63 | CH$_2$—Cyclobutyl | A | m/e: 668 (M$^+$, C$_{39}$H$_{56}$O$_9$) |
| 1.64 | CH$_2$—Cyclobutyl | B | m/e: 668 (M$^+$, C$_{39}$H$_{56}$O$_9$) |
| 1.65 | CH$_2$—Cyclobutyl | A/B | |
| 1.66 | CH$_2$CH(CH$_3$)CH$_2$CH$_3$ | A | m/e: 670 (M$^+$, C$_{39}$H$_{58}$O$_9$) |
| 1.67 | CH$_2$CH(CH$_3$)CH$_2$CH$_3$ | B | m/e: 670 (M$^+$, C$_{39}$H$_{58}$O$_9$) |
| 1.68 | CH$_2$CH(CH$_3$)CH$_2$CH$_3$ | A/B | |
| 1.69 | CH$_2$CH$_2$SCH$_3$ | A | |
| 1.70 | CH$_2$CH$_2$SCH$_3$ | B | |
| 1.71 | CH$_2$CH$_2$SCH$_3$ | A/B | |
| 1.72 | 1-Adamantylmethyl | A | |
| 1.73 | 1-Adamantylmethyl | B | |
| 1.74 | 1-Adamantylmethyl | A/B | |
| 1.75 | CH$_2$—(2-Furyl) | A | |
| 1.76 | CH$_2$—(2-Furyl) | B | |
| 1.77 | CH$_2$—(2-Furyl) | A/B | |
| 1.78 | (+)-2-Methyl-6-isopropyl-cyclohexyl | A | |
| 1.79 | (+)-2-Methyl-6-isopropyl-cyclohexyl | B | |
| 1.80 | (+)-2-Methyl-6-isopropyl-cyclohexyl | A/B | |
| 1.81 | CH$_2$CH$_2$OCOCH$_3$ | A | |
| 1.82 | CH$_2$CH$_2$OCOCH$_3$ | B | |
| 1.83 | CH$_2$CH$_2$OCOCH$_3$ | A/B | m/e: 686 (M$^+$, C$_{38}$H$_{54}$O$_{11}$) |
| 1.84 | CH$_2$CH$_2$OCH$_2$C$_6$H$_5$ | A | |
| 1.85 | CH$_2$CH$_2$OCH$_2$C$_6$H$_5$ | B | |
| 1.86 | CH$_2$CH$_2$OCH$_2$C$_6$H$_5$ | A/B | |
| 1.87 | CH$_2$CH$_2$Cl | A | |
| 1.88 | CH$_2$CH$_2$Cl | B | |
| 1.89 | CH$_2$CH$_2$Cl | A/B | |
| 1.90 | CH$_2$CH$_2$OCH$_2$CH$_2$Cl | A | |
| 1.91 | CH$_2$CH$_2$OCH$_2$CH$_2$Cl | B | |
| 1.92 | CH$_2$CH$_2$OCH$_2$CH$_2$Cl | A/B | |

TABLE 1-continued

Compounds of formula I
in which X = —CH(OR₁)—, R₁ = H and R₂ = CH₃

| Comp. No. | R₃ | Epimer | Physic. constant or Preparation Example |
|---|---|---|---|
| 1.93 | CH₂—(2-Thienyl) | A | |
| 1.94 | CH₂—(2-Thienyl) | B | |
| 1.95 | CH₂—(2-Thienyl) | A/B | |
| 1.96 | (—)-2-Methyl-5-(1-methyl-vinyl)-2-cyclohexen-2-yl | A | |
| 1.97 | (—)-2-Methyl-5-(1-methyl-vinyl)-2-cyclohexen-2-yl | B | |
| 1.98 | (—)-2-Methyl-5-(1-methyl-vinyl)-2-cyclohexen-2-yl | A/B | |
| 1.99 | H | A | |
| 1.100 | H | B | |
| 1.101 | H | A/B | |
| 1.102 | Cyclopentyl | A | |
| 1.103 | Cyclopentyl | B | |
| 1.104 | Cyclopentyl | A/B | |
| 1.105 | Cycloheptyl | A | |
| 1.106 | Cycloheptyl | B | |
| 1.107 | Cycloheptyl | A/B | |
| 1.108 | CH₂C(CH₃)₂CH₂Cl | A | |
| 1.109 | CH₂C(CH₃)₂CH₂Cl | B | |
| 1.110 | CH₂C(CH₃)₂CH₂Cl | A/B | |
| 1.111 | CH(CH₃)CH₂CH₃ (S) | A | |
| 1.112 | CH(CH₃)CH₂CH₃ (S) | B | |
| 1.113 | CH(CH₃)CH₂CH₃ (S) | A/B | |
| 1.114 | CH₂CH₂OCOCH₂Cl | A | |
| 1.115 | CH₂CH₂OCOCH₂Cl | B | |
| 1.116 | CH₂CH₂OCOCH₂Cl | A/B | |
| 1.117 | CH₂CH(CH₂CH₂CH₃)₂ | A | |
| 1.118 | CH₂CH(CH₂CH₂CH₃)₂ | B | |
| 1.119 | CH₂CH(CH₂CH₂CH₃)₂ | A/B | |
| 1.120 | CH(CH₃)CH₂CH₃ (R) | A | |
| 1.121 | CH(CH₃)CH₂CH₃ (R) | B | |
| 1.122 | CH(CH₃)CH₂CH₃ (R) | A/B | |
| 1.123 | 3-Phenoxy-benzyl | A | |
| 1.124 | 3-Phenoxy-benzyl | B | |
| 1.125 | 3-Phenoxy-benzyl | A/B | |
| 1.126 | CH₂—Cyclohexyl | A | m/e: 696 (M⁺, C₄₁H₆₀O₉) |
| 1.127 | CH₂—Cyclohexyl | B | m/e: 696 (M⁺, C₄₁H₆₀O₉) |
| 1.128 | CH₂—Cyclohexyl | A/B | |
| 1.129 | 3,4-Dimethoxybenzyl | A | |
| 1.130 | 3,4-Dimethoxybenzyl | B | |
| 1.131 | 3,4-Dimethoxybenzyl | A/B | |
| 1.132 | CH(CH₃)C₆H₅ (R) | A | |
| 1.133 | CH(CH₃)C₆H₅ (R) | B | |
| 1.134 | CH(CH₃)C₆H₅ (R) | A/B | |
| 1.135 | CH(CH₃)C₆H₅ (S) | A | |
| 1.136 | CH(CH₃)C₆H₅ (S) | B | |
| 1.137 | CH(CH₃)C₆H₅ (S) | A/B | |
| 1.138 | CH₂CH(C₂H₅)₂ | A | |
| 1.139 | CH₂CH(C₂H₅)₂ | B | |
| 1.140 | CH₂CH(C₂H₅)₂ | A/B | |
| 1.141 | CH₂CH(CH₃)₂ | A | |
| 1.142 | CH₂CH(CH₃)₂ | B | |
| 1.143 | CH₂CH(CH₃)₂ | A/B | |
| 1.144 | CH₂C(CH₃)=CH₂ | A | |
| 1.145 | CH₂C(CH₃)=CH₂ | B | |
| 1.146 | CH₂C(CH₃)=CH₂ | A/B | |
| 1.147 | CH₂—1-Methylcyclopropyl | A | |
| 1.148 | CH₂—1-Methylcyclopropyl | B | |
| 1.149 | CH₂—1-Methylcyclopropyl | A/B | |

TABLE 2

Compounds of formula I
in which X = —CH(OR₁)—, R₁ = H und R₂ = C₂H₅

| Comp. No. | R₃ | Epimer | Physic. constant or Preparation Example |
|---|---|---|---|
| 2.1 | CH₃ | A | |
| 2.2 | CH₃ | B | |
| 2.3 | CH₃ | A/B | H1 |
| 2.4 | C₂H₅ | A | |
| 2.5 | C₂H₅ | B | |
| 2.6 | C₂H₅ | A/B | |
| 2.7 | C₃H₇—n | A | |

TABLE 2-continued

Compounds of formula I
in which X = —CH(OR$_1$)—, R$_1$ = H und R$_2$ = C$_2$H$_5$

| Comp. No. | R$_3$ | Epimer | Physic. constant or Preparation Example |
|---|---|---|---|
| 2.8 | C$_3$H$_7$—n | B | |
| 2.9 | C$_3$H$_7$—n | A/B | |
| 2.10 | C$_3$H$_7$—i | A | |
| 2.11 | C$_3$H$_7$—i | B | |
| 2.12 | C$_3$H$_7$—i | A/B | |
| 2.13 | C$_4$H$_9$—n | A | |
| 2.14 | C$_4$H$_9$—n | B | |
| 2.15 | C$_4$H$_9$—n | A/B | |
| 2.16 | C$_6$H$_{13}$—n | A/B | |
| 2.17 | C$_{10}$H$_{21}$—n | A/B | |
| 2.18 | CH$_2$OCH$_3$ | A | |
| 2.19 | CH$_2$OCH$_3$ | B | |
| 2.20 | CH$_2$OCH$_3$ | A/B | |
| 2.21 | CH$_2$CH$_2$OH | A | H19 |
| 2.22 | CH$_2$CH$_2$OH | B | H19 |
| 2.23 | CH$_2$CH$_2$OH | A/B | |
| 2.24 | CH$_2$C(CH$_3$)$_3$ | A | H5 |
| 2.25 | CH$_2$C(CH$_3$)$_3$ | B | H5 |
| 2.26 | CH$_2$C(CH$_3$)$_3$ | A/B | H5 |
| 2.27 | Phenyl | A | m/e: 690 (M$^+$, C$_{41}$H$_{54}$O$_9$) |
| 2.28 | Phenyl | B | m/e: 690 (M$^+$, C$_{41}$H$_{54}$O$_9$) |
| 2.29 | Phenyl | A/B | |
| 2.30 | Benzyl | A | H11 |
| 2.31 | Benzyl | B | H11 |
| 2.32 | Benzyl | A/B | H11 |
| 2.33 | CH$_2$CH$_2$OCH$_3$ | A | |
| 2.34 | CH$_2$CH$_2$OCH$_3$ | B | |
| 2.35 | CH$_2$CH$_2$OCH$_3$ | A/B | |
| 2.36 | CH$_2$CH$_2$OC$_2$H$_5$ | A | H3 |
| 2.37 | CH$_2$CH$_2$OC$_2$H$_5$ | B | H3 |
| 2.38 | CH$_2$CH$_2$OC$_2$H$_5$ | A/B | H3 |
| 2.39 | CH$_2$CH$_2$OCH$_2$CH$_2$OCH$_3$ | A | m/e: 716 (M$^+$, C$_{40}$H$_{60}$O$_{11}$) |
| 2.40 | CH$_2$CH$_2$OCH$_2$CH$_2$OCH$_3$ | B | |
| 2.41 | CH$_2$CH$_2$OCH$_2$CH$_2$OCH$_3$ | A/B | H15 |
| 2.42 | CH$_2$CH$_2$(OCH$_2$CH$_2$)$_2$OH | A | |
| 2.43 | CH$_2$CH$_2$(OCH$_2$CH$_2$)$_2$OH | B | |
| 2.44 | CH$_2$CH$_2$(OCH$_2$CH$_2$)$_2$OH | A/B | H7 |
| 2.45 | CH$_2$CH$_2$(OCH$_2$CH$_2$)$_2$OCOCH$_2$Cl | A | |
| 2.46 | CH$_2$CH$_2$(OCH$_2$CH$_2$)$_2$OCOCH$_2$Cl | B | |
| 2.47 | CH$_2$CH$_2$(OCH$_2$CH$_2$)$_2$OCOCH$_2$Cl | A/B | H9 |
| 2.48 | Cyclohexyl | A | H13 |
| 2.49 | Cyclohexyl | B | H13 |
| 2.50 | Cyclohexyl | A/B | H13 |
| 2.51 | 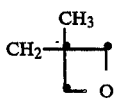 | A | |
| 2.52 | 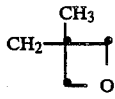 | B | |
| 2.53 | 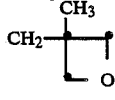 | A/B | H17 |
| 2.54 | CH$_2$Cl$_3$ | A | |
| 2.55 | CH$_2$Cl$_3$ | B | |
| 2.56 | CH$_2$Cl$_3$ | A/B | |
| 2.57 | CH$_2$C(CH$_3$)(CH$_2$Cl)$_2$ | A | m/e: 752 (M$^+$, C$_{40}$H$_{58}$Cl$_2$O$_9$) |
| 2.58 | CH$_2$C(CH$_3$)(CH$_2$Cl)$_2$ | B | m/e: 752 (M$^+$, C$_{40}$H$_{58}$Cl$_2$O$_9$) |
| 2.59 | CH$_2$C(CH$_3$)(CH$_2$Cl)$_2$ | A/B | |
| 2.60 | CH$_2$CBr$_3$ | A | m/e: 880, 878 (M$^+$, C$_{37}$H$_{51}$Br$_3$O$_9$) |
| 2.61 | CH$_2$CBr$_3$ | B | m/e: 880, 878 (M$^+$, C$_{37}$H$_{51}$Br$_3$O$_9$) |
| 2.62 | CH$_2$CBr$_3$ | A/B | |
| 2.63 | CH$_2$—Cyclobutyl | A | m/e: 682 |

TABLE 2-continued

Compounds of formula I
in which X = —CH(OR₁)—, R₁ = H und R₂ = C₂H₅

| Comp. No. | R₃ | Epimer | Physic. constant or Preparation Example |
|---|---|---|---|
| 2.64 | CH₂—Cyclobutyl | B | (M⁺, C₄₀H₅₈O₉) m/e: 682 (M⁺, C₄₀H₅₈O₉) |
| 2.65 | CH₂—Cyclobutyl | A/B | |
| 2.66 | CH₂CH(CH₃)CH₂CH₃ | A | m/e: 684 (M⁺, C₄₀H₆₀O₉) |
| 2.67 | CH₂CH(CH₃)CH₂CH₃ | B | m/e: 684 (M⁺, C₄₀H₆₀O₉) |
| 2.68 | CH₂CH(CH₃)CH₂CH₃ | A/B | |
| 2.69 | CH₂CH₂SCH₃ | A | m/e: 688 (M⁺, C₃₉H₅₆O₉S) |
| 2.70 | CH₂CH₂SCH₃ | B | m/e: 688 M⁺, C₃₉H₅₆O₉S) |
| 2.71 | CH₂CH₂SCH₃ | A/B | |
| 2.72 | 1-Adamantylmethyl | A | m/e: 762 (M⁺, C₄₆H₆₆O₉) |
| 2.73 | 1-Adamantylmethyl | B | m/e: 762 (M⁺, C₄₆H₆₆O₉) |
| 2.74 | 1-Adamantylmethyl | A/B | |
| 2.75 | CH₂—(2-Furyl) | A | m/e: 694 (M⁺, C₄₀H₅₄O₁₀) |
| 2.76 | CH₂—(2-Furyl) | B | m/e: 694 (M⁺, C₄₀H₅₄O₁₀) |
| 2.77 | CH₂—(2-Furyl) | A/B | |
| 2.78 | (+)-2-Methyl-6-isopropyl-cyclohexyl | A | m/e: 752 (M⁺, C₄₅H₆₈O₉) |
| 2.79 | (+)-2-Methyl-6-isopropyl-cyclohexyl | | m/e: 752 (M*, C₄₅H₆₈O₉) |
| 2.80 | (+)-2-Methyl-6-isopropyl-cyclohexyl | A/B | |
| 2.81 | CH₂CH₂OCOCH₃ | A | m/e: 700 (M⁺, C₃₉H₅₆O₁₁) |
| 2.82 | CH₂CH₂OCOCH₃ | B | |
| 2.83 | CH₂CH₂OCOCH₃ | A/B | |
| 2.84 | CH₂CH₂OCH₂C₆H₅ | A | m/e: 748 (M⁺, C₄₄H₆₀O₁₀) |
| 2.85 | CH₂CH₂OCH₂C₆H₅ | B | m/e: 748 (M⁺, C₄₄H₆₀O₁₀) |
| 2.86 | CH₂CH₂OCH₂C₆C₆H₅ | A/B | |
| 2.87 | CH₂CH₂Cl | A | |
| 2.88 | CH₂CH₂Cl | B | |
| 2.89 | CH₂CH₂Cl | A/B | |
| 2.90 | CH₂CH₂OCH₂CH₂Cl | A | |
| 2.91 | CH₂CH₂OCH₂CH₂Cl | B | |
| 2.92 | CH₂CH₂OCH₂CH₂Cl | A/B | |
| 2.93 | CH₂—(2-Thienyl) | A | |
| 2.94 | CH₂—(2-Thienyl) | B | |
| 2.95 | CH₂—(2-Thienyl) | A/B | |
| 2.96 | (—)-2-Methyl-5-(1-methyl-vinyl)-2-cyclohexen-2-yl | A | |
| 2.97 | (—)-2-Methyl-5-(1-methyl-vinyl)-2-cyclohexen-2-yl | B | |
| 2.98 | (—)-2-Methyl-5-(1-methyl-vinyl)-2-cyclohexen-2-yl | A/B | |
| 2.99 | H | A | |
| 2.100 | H | B | |
| 2.101 | H | A/B | m/e: 573 (M⁺, C₃₅H₅₀O₉) |
| 2.102 | Cyclopentyl | A | m/e: 682 (M⁺, C₄₀H₅₈O₉) |
| 2.103 | Cyclopentyl | B | m/e: 682 (M⁺, C₄₀H₅₈O₉) |
| 2.104 | Cyclopentyl | A/B | |
| 2.105 | Cycloheptyl | A | m/e: 710 (M⁺, C₄₂H₆₂O₉) |
| 2.106 | Cycloheptyl | B | m/e: 710 (M⁺, C₄₂H₆₂O₉) |
| 2.107 | Cycloheptyl | A/B | |
| 2.018 | CH₂C(CH₃)₂CH₂Cl | A | m/e: 718 (M⁺, C₄₀H₅₉ClO₉) |
| 2.109 | CH₂C(CH₃)₂CH₂Cl | B | m/e: 718 (M⁺, C₄₀H₅₉ClO₉) |
| 2.110 | CH₂C(CH₃)₂CH₂Cl | A/B | |
| 2.111 | CH(CH₃)CH₂CH₃ (S) | A | m/e: 670 (M⁺, C₃₉H₅₈O₉) |
| 2.112 | CH(CH₃)CH₂CH₃ (S) | B | m/e: 670 (M⁺, C₃₉H₅₈O₉) |
| 2.113 | CH(CH₃)CH₂CH₃ (S) | A/B | |

TABLE 2-continued

Compounds of formula I
in which X = —CH(OR$_1$)—, R$_1$ = H und R$_2$ = C$_2$H$_5$

| Comp. No. | R$_3$ | Epimer | Physic. constant or Preparation Example |
|---|---|---|---|
| 2.114 | CH$_2$CH$_2$OCOCH$_2$Cl | A | m/e: 734 (M$^+$, C$_{39}$H$_{55}$ClO$_{11}$) |
| 2.115 | CH$_2$CH$_2$OCOCH$_2$Cl | B | m/e: 734 (M$^+$, C$_{39}$H$_{55}$ClO$_{11}$) |
| 2.116 | CH$_2$CH$_2$OCOCH$_2$Cl | A/B | |
| 2.117 | CH$_2$CH(CH$_2$CH$_2$CH$_3$)$_2$ | A | m/e: 726 (M$^+$, C$_{43}$H$_{66}$O$_9$) |
| 2.118 | CH$_2$CH(CH$_2$CH$_2$CH$_3$)$_2$ | B | m/e: 726 (M$^+$, C$_{43}$H$_{66}$O$_9$) |
| 2.119 | CH$_2$CH(CH$_2$CH$_2$CH$_3$)$_2$ | A/B | |
| 2.120 | CH(CH$_3$)CH$_2$CH$_3$ (R) | A | m/e: 670 (M$^+$, C$_{39}$H$_{58}$O$_9$) |
| 2.121 | CH(CH$_3$)CH$_2$CH$_3$ (R) | B | m/e: 670 (M$^+$, C$_{39}$H$_{58}$O$_9$) |
| 2.122 | CH(CH$_3$)CH$_2$CH$_3$ (R) | A/B | |
| 2.123 | 3-Phenoxy-benzyl | A | m/e: 796 (M$^+$, C$_{48}$H$_{60}$O$_{10}$) |
| 2.124 | 3-Phenoxy-benzyl | B | m/e: 796 (M$^+$, C$_{48}$H$_{60}$O$_{10}$) |
| 2.125 | 3-Phenoxy-benzyl | A/B | |
| 2.126 | CH$_2$—Cyclohexyl | A | m/e: 710 (M$^+$, C$_{42}$H$_{62}$O$_9$) |
| 2.127 | CH$_2$—Cyclohexyl | B | m/e: 710 (M$^+$, C$_{42}$H$_{62}$O$_9$) |
| 2.128 | CH$_2$—Cyclohexyl | A/B | |
| 2.129 | 3,4-Dimethoxybenzyl | A | m/e: 764 (M$^+$, C$_{44}$H$_{60}$O$_{11}$) |
| 2.130 | 3,4-Dimethoxybenzyl | B | m/e: 764 (M$^+$, C$_{44}$H$_{60}$O$_{11}$) |
| 2.131 | 3,4-Dimethoxybenzyl | A/B | |
| 2.132 | CH(CH$_3$)C$_6$H$_5$ (R) | A | m/e: 718 (M$^+$, C$_{43}$H$_{58}$O$_9$) |
| 2.133 | CH(CH$_3$)C$_6$H$_5$ (R) | B | m/e: 718 (M$^+$, C$_{43}$H$_{58}$O$_9$) |
| 2.134 | CH(CH$_3$)C$_6$H$_5$ (R) | A/B | |
| 2.135 | CH(CH$_3$)C$_6$H$_5$ (R) | A | m/e: 718 (M$^+$, C$_{43}$H$_{58}$O$_9$) |
| 2.136 | CH(CH$_3$)C$_6$H$_5$ (S) | B | m/e: 718 (M$^+$, C$_{43}$H$_{58}$O$_9$) |
| 2.137 | CH(CH$_3$)C$_6$H$_5$ (S) | A/B | |
| 2.138 | CH$_2$CH(C$_2$H$_5$)$_2$ | A | |
| 2.139 | CH$_2$CH(C$_2$H$_5$)$_2$ | B | |
| 2.140 | CH$_2$CH(C$_2$H$_5$)$_2$ | A/B | |
| 2.141 | CH$_2$CH(CH$_3$)$_2$ | A | m/e: 670 (M$^+$, C$_{39}$H$_{58}$O$_9$) |
| 2.142 | CH$_2$CH(CH$_3$)$_2$ | B | m/e: 670 (M$^+$, C$_{39}$H$_{58}$O$_9$) |
| 2.143 | CH$_2$CH(CH$_3$)$_2$ | A/B | |
| 2.144 | CH$_2$C(CH$_3$)=CH$_2$ | A | |
| 2.145 | CH$_2$C(CH$_3$)=CH$_2$ | B | |
| 2.146 | CH$_2$C(CH$_3$)=CH$_2$ | A/B | |
| 2.147 | CH$_2$—1-Methylcyclopropyl | A | |
| 2.148 | CH$_2$—1-Methylcyclopropyl | B | |
| 2.149 | CH$_2$—1-Methylcyclopropyl | A/B | | and the corresponding compounds 3.1 to 3.149 in which X, R$_1$ and R$_3$ have the meanings given for compounds 2.1 to 2.149 in Table 2, and R$_2$ represents isopropyl; and also the corresponding compounds 4.1 to 4.149 in which X, R$_1$ and R$_3$ have the meanings given for compounds 2.1 to 2.149 in Table 2, and R$_2$ represents sec.-butyl.

TABLE 3

Compounds of formula I
in which X = —CH(OR$_1$)—, R$_1$ = Si(CH$_3$)$_2$C(CH$_3$)$_3$ and R$_2$ = CH$_3$

| Comp. No. | R$_3$ | Epimer | Physic. constant or Preparation Example |
|---|---|---|---|
| 5.1 | CH$_3$ | A | |
| 5.2 | CH$_3$ | B | |
| 5.3 | CH$_3$ | A/B | |
| 5.4 | C$_2$H$_5$ | A | |
| 5.5 | C$_2$H$_5$ | B | |
| 5.6 | C$_2$H$_5$ | A/B | |
| 5.7 | C$_3$H$_7$—n | A | |
| 5.8 | C$_3$H$_7$—n | B | |
| 5.9 | C$_3$H$_7$—n | A/B | |
| 5.10 | C$_3$H$_7$—i | A | |
| 5.11 | C$_3$H$_7$—i | B | |

TABLE 3-continued

Compounds of formula I
in which X = —CH(OR$_1$)—, R$_1$ = Si(CH$_3$)$_2$C(CH$_3$)$_3$ and R$_2$ = CH$_3$

| Comp. No. | R$_3$ | Epimer | Physic. constant or Preparation Example |
|---|---|---|---|
| 5.12 | C$_3$H$_7$—i | A/B | |
| 5.13 | C$_4$H$_9$—n | A | |
| 5.14 | C$_4$H$_9$—n | B | |
| 5.15 | C$_4$H$_9$—n | A/B | |
| 5.16 | C$_6$H$_{13}$—n | A/B | |
| 5.17 | C$_{10}$H$_{21}$—n | A/B | |
| 5.18 | CH$_2$OCH$_3$ | A | |
| 5.19 | CH$_2$OCH$_3$ | B | |
| 5.20 | CH$_2$OCH$_3$ | A/B | |
| 5.21 | CH$_2$CH$_2$OH | A | |
| 5.22 | CH$_2$CH$_2$OH | B | |
| 5.23 | CH$_2$CH$_2$OH | A/B | |
| 5.24 | CH$_2$C(CH$_3$)$_3$ | A | m/e: 784 (M$^+$, C$_{45}$H$_{72}$O$_9$Si) |
| 5.25 | CH$_2$C(CH$_3$)$_3$ | B | m/e: 784 (M$^+$, C$_{45}$H$_{72}$O$_9$Si) |
| 5.26 | CH$_2$C(CH$_3$)$_3$ | A/B | |
| 5.27 | Phenyl | A | |
| 5.28 | Phenyl | B | |
| 5.29 | Phenyl | A/B | |
| 5.30 | Benzyl | A | |
| 5.31 | Benzyl | B | |
| 5.32 | Benzyl | A/B | |
| 5.33 | CH$_2$CH$_2$OCH$_3$ | A | |
| 5.34 | CH$_2$CH$_2$OCH$_3$ | B | |
| 5.35 | CH$_2$CH$_2$OCH$_3$ | A/B | |
| 5.36 | CH$_2$CH$_2$OC$_2$H$_5$ | A | m/e: 786 (M$^+$, C$_{44}$H$_{71}$O$_{10}$Si) |
| 5.37 | CH$_2$CH$_2$OC$_2$H$_5$ | B | m/e: 786 (M$^+$, C$_{44}$H$_{71}$O$_{10}$Si) |
| 5.38 | CH$_2$CH$_2$OC$_2$H$_5$ | A/B | |
| 5.39 | CH$_2$CH$_2$OCH$_2$CH$_2$OCH$_3$ | A | |
| 5.40 | CH$_2$CH$_2$OCH$_2$CH$_2$OCH$_3$ | B | |
| 5.41 | CH$_2$CH$_2$OCH$_2$CH$_2$OCH$_3$ | A/B | |
| 5.42 | CH$_2$CH$_2$(OCH$_2$CH$_2$)$_2$OH | A | |
| 5.43 | CH$_2$CH$_2$(OCH$_2$CH$_2$)$_2$OH | B | |
| 5.44 | CH$_2$CH$_2$(OCH$_2$CH$_2$)$_2$OH | A/B | |
| 5.45 | CH$_2$CH$_2$(OCH$_2$CH$_2$)$_2$OCOCH$_2$Cl | A | |
| 5.46 | CH$_2$CH$_2$(OCH$_2$CH$_2$)$_2$OCOCH$_2$Cl | B | |
| 5.47 | CH$_2$CH$_2$(OCH$_2$CH$_2$)$_2$OCOCH$_2$Cl | A/B | |
| 5.48 | Cyclohexyl | A | m/e: 796 (M$^+$, C$_{46}$H$_{72}$O$_9$Si) |
| 5.49 | Cyclohexyl | B | m/e: 796 (M$^+$, C$_{46}$H$_{72}$O$_9$Si) |
| 5.50 | Cyclohexyl | A/B | |
| 5.51 | 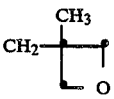 | A | |
| 5.52 | 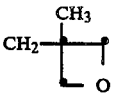 | B | |
| 5.53 | 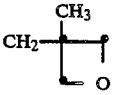 | A/B | |
| 5.54 | CH$_2$Cl$_3$ | A | |
| 5.55 | CH$_2$Cl$_3$ | B | |
| 5.56 | CH$_2$Cl$_3$ | A/B | |
| 5.57 | CH$_2$C(CH$_3$)(CH$_2$Cl)$_2$ | A | |
| 5.58 | CH$_2$C(CH$_3$)(CH$_2$Cl)$_2$ | B | |
| 5.59 | CH$_2$C(CH$_3$)(CH$_2$Cl)$_2$ | A/B | |
| 5.60 | CH$_2$CBr$_3$ | A | |
| 5.61 | CH$_2$CBr$_3$ | B | |
| 5.62 | CH$_2$CBr$_3$ | A/B | |
| 5.63 | CH$_2$—Cyclobutyl | A | m/e: 782 (M$^+$, C$_{45}$H$_{70}$O$_8$Si) |
| 5.64 | CH$_2$—Cyclobutyl | B | m/e: 782 (M$^+$, C$_{45}$H$_{70}$O$_8$Si) |
| 5.65 | CH$_2$—Cyclobutyl | A/B | |
| 5.66 | CH$_2$CH(CH$_3$)CH$_2$CH$_3$ | A | m/e: 784 |

TABLE 3-continued

Compounds of formula I
in which X = —CH(OR$_1$)—, R$_1$ = Si(CH$_3$)$_2$C(CH$_3$)$_3$ and R$_2$ = CH$_3$

| Comp. No. | R$_3$ | Epimer | Physic. constant or Preparation Example |
|---|---|---|---|
| 5.67 | CH$_2$CH(CH$_3$)CH$_2$CH$_3$ | B | (M$^+$, C$_{45}$H$_{72}$O$_9$Si) m/e: 784 |
| 5.68 | CH$_2$CH(CH$_3$)CH$_2$CH$_3$ | A/B | (M$^+$, C$_{45}$H$_{72}$O$_9$Si) |
| 5.69 | CH$_2$CH$_2$SCH$_3$ | A | |
| 5.70 | CH$_2$CH$_2$SCH$_3$ | B | |
| 5.71 | CH$_2$CH$_2$SCH$_3$ | A/B | |
| 5.72 | 1-Adamantylmethyl | A | |
| 5.73 | 1-Adamantylmethyl | B | |
| 5.74 | 1-Adamantylmethyl | A/B | |
| 5.75 | CH$_2$—(2-Furyl) | A | |
| 5.76 | CH$_2$—(2-Furyl) | B | |
| 5.77 | CH$_2$—(2-Furyl) | A/B | |
| 5.78 | (+)-2-Methyl-6-isopropyl-cyclohexyl | A | |
| 5.79 | (+)-2-Methyl-6-isopropyl-cyclohexyl | B | |
| 5.80 | (+)-2-Methyl-6-isopropyl-cyclohexyl | A/B | |
| 5.81 | CH$_2$CH$_2$OCOCH$_3$ | A | |
| 5.82 | CH$_2$CH$_2$OCOCH$_3$ | B | |
| 5.83 | CH$_2$CH$_2$OCOCH$_3$ | A/B | |
| 5.84 | CH$_2$CH$_2$OCH$_2$C$_6$H$_5$ | A | |
| 5.78 | (+)-2-Methyl-6-isopropyl-cyclohexyl | A | |
| 5.79 | (+)-2-Methyl-6-isopropyl-cyclohexyl | B | |
| 5.80 | (+)-2-Methyl-6-isopropyl-cyclohexyl | A/B | |
| 5.81 | CH$_2$CH$_2$OCOCH$_3$ | A | |
| 5.82 | CH$_2$CH$_2$OCOCH$_3$ | B | |
| 5.83 | CH$_2$CH$_2$OCOCH$_3$ | A/B | |
| 5.84 | CH$_2$CH$_2$OCH$_2$C$_6$H$_5$ | A | |
| 5.85 | CH$_2$CH$_2$OCH$_2$C$_6$H$_5$ | B | |
| 5.86 | CH$_2$CH$_2$OCH$_2$C$_6$H$_5$ | A/B | |
| 5.87 | CH$_2$CH$_2$Cl | A | |
| 5.88 | CH$_2$CH$_2$Cl | B | |
| 5.89 | CH$_2$CH$_2$Cl | A/B | |
| 5.90 | CH$_2$CH$_2$OCH$_2$CH$_2$Cl | A | |
| 5.91 | CH$_2$CH$_2$OCH$_2$CH$_2$Cl | B | |
| 5.92 | CH$_2$CH$_2$OCH$_2$CH$_2$Cl | A/B | |
| 5.93 | CH$_2$—(2-Thienyl) | A | |
| 5.94 | CH$_2$—(2-Thienyl) | B | |
| 5.95 | CH$_2$—(2-Thienyl) | A/B | |
| 5.96 | (−)-2-Methyl-5-(1-methyl-vinyl)-2-cyclohexen-2-yl | A | |
| 5.97 | (−)-2-Methyl-5-(1-methyl-vinyl)-2-cyclohexen-2-yl | B | |
| 5.98 | (−)-2-Methyl-5-(1-methyl-vinyl)-2-cyclohexen-2-yl | A/B | |
| 5.99 | H | A | |
| 5.100 | H | B | |
| 5.101 | H | A/B | |
| 5.102 | Cyclopentyl | A | |
| 5.103 | Cyclopentyl | B | |
| 5.104 | Cyclopentyl | A/B | |
| 5.105 | Cycloheptyl | A | |
| 5.106 | Cycloheptyl | B | |
| 5.107 | Cycloheptyl | A/B | |
| 5.108 | CH$_2$C(CH$_3$)$_2$CH$_2$Cl | A | |
| 5.109 | CH$_2$C(CH$_3$)$_2$CH$_2$Cl | B | |
| 5.110 | CH$_2$C(CH$_3$)$_2$CH$_2$Cl | A/B | |
| 5.111 | CH(CH$_3$)CH$_2$CH$_3$ (S) | A | |
| 5.112 | CH(CH$_3$)CH$_2$CH$_3$ (S) | B | |
| 5.113 | CH(CH$_3$)CH$_2$CH$_3$ (S) | A/B | |
| 5.114 | CH$_2$CH$_2$OCOCH$_2$Cl | A | |
| 5.115 | CH$_2$CH$_2$OCOCH$_2$Cl | B | |
| 5.116 | CH$_2$CH$_2$OCOCH$_2$Cl | A/B | |
| 5.117 | CH$_2$CH(CH$_2$CH$_2$CH$_3$)$_2$ | A | |
| 5.118 | CH$_2$CH(CH$_2$CH$_2$CH$_3$)$_2$ | B | |
| 5.119 | CH$_2$CH(CH$_2$CH$_2$CH$_3$)$_2$ | A/B | |
| 5.120 | CH(CH$_3$)CH$_2$CH$_3$ (R) | A | |
| 5.121 | CH(CH$_3$)CH$_2$CH$_3$ (R) | B | |
| 5.122 | CH(CH$_3$)CH$_2$CH$_3$ (R) | A/B | |
| 5.123 | 3-Phenoxy-benzyl | A | |
| 5.124 | 3-Phenoxy-benzyl | B | |
| 5.125 | 3-Phenoxy-benzyl | A/B | |
| 5.119 | CH$_2$CH(CH$_2$CH$_2$CH$_3$)$_2$ | A/B | |

TABLE 3-continued

Compounds of formula I
in which X = —CH(OR₁)—, R₁ = Si(CH₃)₂C(CH₃)₃ and R₂ = CH₃

| Comp. No. | R₃ | Epimer | Physic. constant or Preparation Example |
|---|---|---|---|
| 5.120 | CH(CH₃)CH₂CH₃ (R) | A | |
| 5.121 | CH(CH₃)CH₂CH₃ (R) | B | |
| 5.122 | CH(CH₃)CH₂CH₃ (R) | A/B | |
| 5.123 | 3-Phenoxy-benzyl | A | |
| 5.124 | 3-Phenoxy-benzyl | B | |
| 5.125 | 3-Phenoxy-benzyl | A/B | |
| 5.126 | CH₂—Cyclohexyl | A | m/e: 810 (M⁺, C₄₇H₇₄O₉Si) |
| 5.127 | CH₂—Cyclohexyl | B | m/e: 810 (M⁺, C₄₇H₇₄O₉Si) |
| 5.128 | CH₂—Cyclohexyl | A/B | |
| 5.129 | 3,4-Dimethoxybenzyl | A | |
| 5.130 | 3,4-Dimethoxybenzyl | B | |
| 5.131 | 3,4-Dimethoxybenzyl | A/B | |
| 5.132 | CH(CH₃)C₆H₅ (R) | A | |
| 5.133 | CH(CH₃)C₆H₅ (R) | B | |
| 5.134 | CH(CH₃)C₆H₅ (R) | A/B | |
| 5.135 | CH(CH₃)C₆H₅ (S) | A | |
| 5.136 | CH(CH₃)C₆H₅ (S) | B | |
| 5.137 | CH(CH₃)C₆H₅ (S) | A/B | |
| 5.138 | CH₂CH(C₂H₅)₂ | A | |
| 5.139 | CH₂CH(C₂H₅)₂ | B | |
| 5.140 | CH₂CH(C₂H₅)₂ | A/B | |
| 5.141 | CH₂CH(CH₃)₂ | A | |
| 5.142 | CH₂CH(CH₃)₂ | B | |
| 5.143 | CH₂CH(CH₃)₂ | A/B | |
| 5.144 | CH₂C(CH₃)=CH₂ | A | |
| 5.145 | CH₂C(CH₃)=CH₂ | B | |
| 5.146 | CH₂C(CH₃)=CH₂ | A/B | |
| 5.147 | CH₂—1-Methylcyclopropyl | A | |
| 5.148 | CH₂—1-Methylcyclopropyl | B | |
| 5.149 | CH₂—1-Methylcyclopropyl | A/B | |

TABLE 4

Compounds of formula I
in which X = —CH(OR₁)—, R₁ = Si(CH₃)₂C(CH₃)₃ and R₂ = C₂H₅

| Comp. No. | R₃ | Epimer | Physic. constant or Preparation Example |
|---|---|---|---|
| 6.1 | CH₃ | A | |
| 6.2 | CH₃ | B | |
| 6.3 | CH₃ | A/B | |
| 6.4 | C₂H₅ | A | |
| 6.5 | C₂H₅ | B | |
| 6.6 | C₂H₅ | A/B | |
| 6.7 | C₃H₇—n | A | |
| 6.8 | C₃H₇—n | B | |
| 6.9 | C₃H₇—n | A/B | |
| 6.10 | C₃H₇—i | A | |
| 6.11 | C₃H₇—i | B | |
| 6.12 | C₃H₇—i | A/B | |
| 6.13 | C₄H₉—n | A | |
| 6.14 | C₄H₉—n | B | |
| 6.15 | C₄H₉—n | A/B | |
| 6.16 | C₆H₁₃—n | A/B | |
| 6.17 | C₁₀H₂₁—n | A/B | |
| 6.18 | CH₂OCH₃ | A | |
| 6.19 | CH₂OCH₃ | B | |
| 6.20 | CH₂OCH₃ | A/B | |
| 6.21 | CH₂CH₂OH | A | |
| 6.22 | CH₂CH₂OH | B | |
| 6.23 | CH₂CH₂OH | A/B | H18 |
| 6.24 | CH₂C(CH₃)₃ | A | H4 |
| 6.25 | CH₂C(CH₃)₃ | B | H4 |
| 6.26 | CH₂C(CH₃)₃ | A/B | H4 |
| 6.27 | Phenyl | A | |
| 6.28 | Phenyl | B | |
| 6.29 | Phenyl | A/B | |
| 6.30 | Benzyl | A | H10 |
| 6.31 | Benzyl | B | H10 |
| 6.32 | Benzyl | A/B | H10 |
| 6.33 | CH₂CH₂OCH₃ | A | |
| 6.34 | CH₂CH₂OCH₃ | B | |
| 6.35 | CH₂CH₂OCH₃ | A/B | |
| 6.36 | CH₂CH₂OC₂H₅ | A | H2 |
| 6.37 | CH₂CH₂OC₂H₅ | B | H2 |

TABLE 4-continued

Compounds of formula I
in which X = —CH(OR$_1$)—, R$_1$ = Si(CH$_3$)$_2$C(CH$_3$)$_3$ and R$_2$ = C$_2$H$_5$

| Comp. No. | R$_3$ | Epimer | Physic. constant or Preparation Example |
|---|---|---|---|
| 6.38 | CH$_2$CH$_2$OC$_2$H$_5$ | A/B | |
| 6.39 | CH$_2$CH$_2$OCH$_2$CH$_2$OCH$_3$ | A | |
| 6.40 | CH$_2$CH$_2$OCH$_2$CH$_2$OCH$_3$ | B | |
| 6.41 | CH$_2$CH$_2$OCH$_2$CH$_2$OCH$_3$ | A/B | H14 |
| 6.42 | CH$_2$CH$_2$(OCH$_2$CH$_2$)$_2$OH | A | |
| 6.43 | CH$_2$CH$_2$(OCH$_2$CH$_2$)$_2$OH | B | |
| 6.44 | CH$_2$CH$_2$(OCH$_2$CH$_2$)$_2$OH | A/B | H6 |
| 6.45 | CH$_2$CH$_2$(OCH$_2$CH$_2$)$_2$OCOCH$_2$Cl | A | |
| 6.46 | CH$_2$CH$_2$(OCH$_2$CH$_2$)$_2$OCOCH$_2$Cl | B | |
| 6.47 | CH$_2$CH$_2$(OCH$_2$CH$_2$)$_2$OCOCH$_2$Cl | A/B | H8 |
| 6.48 | Cyclohexyl | A | H12 |
| 6.49 | Cyclohexyl | B | H12 |
| 6.50 | Cyclohexyl | A/B | H12 |
| 6.51 | 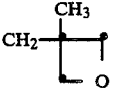 | A | |
| 6.52 | 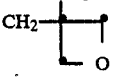 | B | |
| 6.53 | 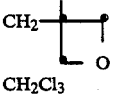 | A/B | H16 |
| 6.54 | CH$_2$Cl$_3$ | A | |
| 6.55 | CH$_2$Cl$_3$ | B | |
| 6.56 | CH$_2$Cl$_3$ | A/B | |
| 6.57 | CH$_2$C(CH$_3$)(CH$_2$Cl)$_2$ | A | m/e: 868 (M$^+$, C$_{46}$H$_{72}$Cl$_2$O$_9$Si) |
| 6.58 | CH$_2$C(CH$_3$)(CH$_2$Cl)$_2$ | B | m/e: 868 (M$^+$, C$_{46}$H$_{72}$Cl$_2$O$_9$Si) |
| 6.59 | CH$_2$C(CH$_3$)(CH$_2$Cl)$_2$ | A/B | |
| 6.60 | CH$_2$CBr$_3$ | A | m/e: 992, 994 (M$^+$, C$_{43}$H$_{65}$Br$_3$O$_9$Si) |
| 6.61 | CH$_2$CBr$_3$ | B | m/e: 992, 994 (M$^+$, C$_{43}$H$_{65}$Br$_3$O$_9$Si) |
| 6.62 | CH$_2$CBr$_3$ | A/B | |
| 6.63 | CH$_2$—Cyclobutyl | A | m/e: 796 (M$^+$, C$_{46}$H$_{72}$O$_8$Si) |
| 6.64 | CH$_2$—Cyclobutyl | B | m/e: 796 (M$^+$, C$_{46}$H$_{72}$O$_8$Si) |
| 6.65 | CH$_2$—Cyclobutyl | A/B | |
| 6.66 | CH$_2$CH(CH$_3$)CH$_2$CH$_3$ | A | m/e: 798 (M$^+$, C$_{46}$H$_{74}$O$_9$Si) |
| 6.67 | CH$_2$CH(CH$_3$)CH$_2$CH$_3$ | B | m/e: 798 (M$^+$, C$_{46}$H$_{74}$O$_9$Si) |
| 6.68 | CH$_2$CH(CH$_3$)CH$_2$CH$_3$ | A/B | |
| 6.69 | CH$_2$CH$_2$SCH$_3$ | A | |
| 6.70 | CH$_2$CH$_2$SCH$_3$ | B | |
| 6.71 | CH$_2$CH$_2$SCH$_3$ | A/B | |
| 6.72 | 1-Adamantylmethyl | A | m/e: 876 (M$^+$, C$_{52}$H$_{80}$O$_9$Si) |
| 6.73 | 1-Adamantylmethyl | B | m/e: 876 (M$^+$, C$_{52}$H$_{80}$O$_9$Si) |
| 6.74 | 1-Adamantylmethyl | A/B | |
| 6.75 | CH$_2$—(2-Furyl) | A | m/e: 808 (M$^+$, C$_{46}$H$_{68}$O$_{10}$Si) |
| 6.76 | CH$_2$—(2-Furyl) | B | m/e: 808 (M$^+$, C$_{46}$H$_{68}$O$_{10}$Si) |
| 6.77 | CH$_2$—(2-Furyl) | A/B | |
| 6.78 | (+)-2-Methyl-6-isopropyl-cyclohexyl | A | m/e: 866 (M$^+$, C$_{51}$H$_{82}$O$_9$Si) |
| 6.79 | (+)-2-Methyl-6-isopropyl-cyclohexyl | B | m/e: 866 (M$^+$, C$_{51}$H$_{82}$O$_9$Si) |
| 6.80 | (+)-2-Methyl-6-isopropyl-cyclohexyl | A/B | |
| 6.81 | CH$_2$CH$_2$OCOCH$_3$ | A | |
| 6.82 | CH$_2$CH$_2$OCOCH$_3$ | B | |
| 6.83 | CH$_2$CH$_2$OCOCH$_3$ | A/B | |
| 6.84 | CH$_2$CH$_2$OCH$_2$C$_6$H$_5$ | A | m/e: 862 (M$^+$, C$_{50}$H$_{74}$O$_{10}$Si) |
| 6.85 | CH$_2$CH$_2$OCH$_2$C$_6$H$_5$ | B | m/e: 862 |

TABLE 4-continued

Compounds of formula I
in which X = —CH(OR$_1$)—, R$_1$ = Si(CH$_3$)$_2$C(CH$_3$)$_3$ and R$_2$ = C$_2$H$_5$

| Comp. No. | R$_3$ | Epimer | Physic. constant or Preparation Example |
|---|---|---|---|
| 6.86 | CH$_2$CH$_2$OCH$_2$C$_6$H$_5$ | A/B | (M$^+$, C$_{50}$H$_{74}$O$_{10}$Si) |
| 6.87 | CH$_2$CH$_2$Cl | A | |
| 6.88 | CH$_2$CH$_2$Cl | B | |
| 6.89 | CH$_2$CH$_2$Cl | A/B | |
| 6.90 | CH$_2$CH$_2$OCH$_2$CH$_2$Cl | A | |
| 6.91 | CH$_2$CH$_2$OCH$_2$CH$_2$Cl | B | |
| 6.92 | CH$_2$CH$_2$OCH$_2$CH$_2$Cl | A/B | |
| 6.93 | CH$_2$—(2-Thienyl) | A | |
| 6.94 | CH$_2$—(2-Thienyl) | B | |
| 6.95 | CH$_2$—(2-Thienyl) | A/B | |
| 6.96 | (—)-2-Methyl-5-(1-methyl-vinyl)-2-cyclohexen-2-yl | A | |
| 6.97 | (—)-2-Methyl-5-(1-methyl-vinyl)-2-cyclohexen-2-yl | B | |
| 6.98 | (—)-2-Methyl-5-(1-methyl-vinyl)-2-cyclohexen-2-yl | A/B | |
| 6.99 | H | A | |
| 6.100 | H | B | |
| 6.101 | H | A/B | m/e: 728 (M$^+$, C$_{41}$H$_{64}$O$_9$Si) |
| 6.102 | Cyclopentyl | A | m/e: 796 (M$^+$, C$_{46}$H$_{72}$O$_9$Si) |
| 6.103 | Cyclopentyl | B | m/e: 796 (M$^+$, C$_{46}$H$_{72}$O$_9$Si) |
| 6.104 | Cyclopentyl | A/B | |
| 6.105 | Cycloheptyl | A | |
| 6.106 | Cycloheptyl | B | |
| 6.107 | Cycloheptyl | A/B | |
| 6.108 | CH$_2$C(CH$_3$)$_2$CH$_2$Cl | A | m/e: 832 (M$^+$, C$_{46}$H$_{73}$ClO$_9$Si) |
| 6.109 | CH$_2$C(CH$_3$)$_2$CH$_2$Cl | B | m/e: 832 (M$^+$, C$_{46}$H$_{73}$ClO$_9$Si) |
| 6.110 | CH$_2$C(CH$_3$)$_2$CH$_2$Cl | A/B | |
| 6.111 | CH(CH$_3$)CH$_2$CH$_3$ (S) | A | m/e: 784 (M$^+$, C$_{45}$H$_{72}$O$_9$Si) |
| 6.112 | CH(CH$_3$)CH$_2$CH$_3$ (S) | B | m/e: 784 (M$^+$, C$_{45}$H$_{72}$O$_9$Si) |
| 6.113 | CH(CH$_3$)CH$_2$CH$_3$ (S) | A/B | |
| 6.114 | CH$_2$CH$_2$OCOCH$_2$Cl | A | m/e: 848 (M$^+$, C$_{45}$H$_{69}$ClO$_{11}$Si) |
| 6.115 | CH$_2$CH$_2$OCOCH$_2$Cl | B | m/e: 848 (M$^+$, C$_{45}$H$_{69}$ClO$_{11}$Si) |
| 6.116 | CH$_2$CH$_2$OCOCH$_2$Cl | A/B | |
| 6.117 | CH$_2$CH(CH$_2$CH$_2$CH$_3$)$_2$ | A | m/e: 840 (M$^+$, C$_{49}$H$_{80}$O$_9$Si) |
| 6.118 | CH$_2$CH(CH$_2$CH$_2$CH$_3$)$_2$ | B | m/e: 840 (M$^+$, C$_{49}$H$_{80}$O$_9$Si) |
| 6.119 | CH$_2$CH(CH$_2$CH$_2$CH$_3$)$_2$ | A/B | |
| 6.120 | CH(CH$_3$)CH$_2$CH$_3$ (R) | A | m/e: 784 (M$^+$, C$_{45}$H$_{72}$O$_9$Si) |
| 6.121 | CH(CH$_3$)CH$_2$CH$_3$ (R) | B | m/e: 784 (M$^+$, C$_{45}$H$_{72}$O$_9$Si) |
| 6.122 | CH(CH$_3$)CH$_2$CH$_3$ (R) | A/B | |
| 6.123 | 3-Phenoxy-benzyl | A | m/e: 910 (M$^+$, C$_{54}$H$_{74}$O$_{10}$Si) |
| 6.124 | 3-Phenoxy-benzyl | B | m/e: 910 (M$^+$, C$_{54}$H$_{74}$O$_{10}$Si) |
| 6.125 | 3-Phenoxy-benzyl | A/B | |
| 6.126 | CH$_2$—Cyclohexyl | A | m/e: 824 (M$^+$, C$_{48}$H$_{76}$O$_9$Si) |
| 6.127 | CH$_2$—Cyclohexyl | B | m/e: 824 (M$^+$, C$_{48}$H$_{76}$O$_9$Si) |
| 6.128 | CH$_2$—Cyclohexyl | A/B | |
| 6.129 | 3,4-Dimethoxybenzyl | A | m/e: 878 (M$^+$, C$_{50}$H$_{74}$O$_{11}$Si) |
| 6.130 | 3,4-Dimethoxybenzyl | B | m/e: 878 (M$^+$, C$_{50}$H$_{74}$O$_{11}$Si) |
| 6.131 | 3,4-Dimethoxybenzyl | A/B | |
| 6.132 | CH(CH$_3$)C$_6$H$_5$ (R) | A | m/e: 832 (M$^+$, C$_{49}$H$_{72}$O$_9$Si) |
| 6.133 | CH(CH$_3$)C$_6$H$_5$ (R) | B | m/e: 832 (M$^+$, C$_{49}$H$_{72}$O$_9$Si) |
| 6.134 | CH(CH$_3$)C$_6$H$_5$ (R) | A/B | |
| 6.135 | CH(CH$_3$)C$_6$H$_5$ (S) | A | m/e: 832 (M$^+$, C$_{49}$H$_{72}$O$_9$Si) |
| 6.136 | CH(CH$_3$)C$_6$H$_5$ (S) | B | m/e: 832 (M$^+$, C$_{49}$H$_{72}$O$_9$Si) |

TABLE 4-continued

Compounds of formula I
in which X = —CH(OR$_1$)—, R$_1$ = Si(CH$_3$)$_2$C(CH$_3$)$_3$ and R$_2$ = C$_2$H$_5$

| Comp. No. | R$_3$ | Epimer | Physic. constant or Preparation Example |
|---|---|---|---|
| 6.137 | CH(CH$_3$)C$_6$H$_5$ (S) | A/B | |
| 6.138 | CH$_2$CH(C$_2$H$_5$)$_2$ | A | |
| 6.139 | CH$_2$CH(C$_2$H$_5$)$_2$ | B | |
| 6.140 | CH$_2$CH(C$_2$H$_5$)$_2$ | A/B | |
| 6.141 | CH$_2$CH(CH$_3$)$_2$ | A | m/e: 784 (M$^+$, C$_{45}$H$_{72}$O$_9$Si) |
| 6.142 | CH$_2$CH(CH$_3$)$_2$ | B | m/e: 784 (M$^+$, C$_{45}$H$_{72}$O$_9$Si) |
| 6.143 | CH$_2$CH(CH$_3$)$_2$ | A/B | |
| 6.144 | CH$_2$C(CH$_3$)=CH$_2$ | A | |
| 6.145 | CH$_2$C(CH$_3$)=CH$_2$ | B | |
| 6.146 | CH$_2$C(CH$_3$)=CH$_2$ | A/B | |
| 6.147 | CH$_2$—1-Methylcyclopropyl | A | |
| 6.148 | CH$_2$—1-Methylcyclopropyl | B | |
| 6.149 | CH$_2$—1-Methylcyclopropyl | A/B | | and the corresponding compounds 7.1 to 7.149 in which X, R$_1$ and R$_3$ have the meanings given for compounds 6.1 to 6.149 in Table 6, and R$_2$ represents isopropyl; and also the corresponding compounds 8.1 to 8.149 in which X, R$_1$ and R$_3$ have the meanings given for compounds 6.1 to 6.149 in Table 6, and R$_2$ represents sec.-butyl.

Formulation examples for active ingredients of formula I
(throughout, percentages are by weight)

| Wettable powders | (a) | (b) | (c) |
|---|---|---|---|
| active ingredient from the Tables | 25% | 50% | 75% |
| sodium lignosulphonate | 5% | 5% | — |
| sodium laurylsulphate | 3% | — | 5% |
| sodium diisobutylnaphthalene-sulphonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| Emulsifiable concentrate | |
|---|---|
| active ingredient from the Tables | 10% |
| octylphenol polyethylene glycol ether (4-5 moles of ethylene oxide) | 3% |
| calcium dodecylbenzenesulphonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| active ingredient from the Tables | 5% | 8% |
| talcum | 95% | — |
| kaolin | — | 92% |

Ready for use dusts are obtained by mixing the active ingredient with the carrier and grinding the mixture in a suitable mill.

| Extruder granulate | |
|---|---|
| active ingredient from the Tables | 10% |
| sodium lignosulphonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| Tablets or boli | |
|---|---|
| I an active ingredient from the Tables | 33.0% |
| methyl cellulose | 0.80% |
| highly dispersed silicic acid | 0.80% |
| maize starch | 8.40% |

The methyl cellulose is stirred in water and allowed to swell; the silicic acid is then stirred in to give a homogeneous suspension. The active ingredient and the maize starch are mixed and the aqueous suspension is added to this mixture, which is kneaded to a paste. This paste is granulated through a sieve (12M mesh width) and the granulate is then dried.

| II crystalline lactose | 22.50% |
|---|---|
| maize starch | 17.00% |
| microcrystalline cellulose | 16.50% |
| magnesium stearate | 1.00% |

All four adjuvants are thoroughly mixed.
Phases I and II are mixed and compressed to form tablets or boli.

| Injectable formulations | |
|---|---|
| A. Oily vehicle (slow release) | |
| an active ingredient from the Tables | 0.1–1.0 g |
| groundnut oil | ad 100 ml |
| an active ingredient from the Tables | 0.1–1.0 g |
| sesame oil | ad 100 ml |

Preparation: The active ingredient is dissolved in a portion of the oil while stirring and, if necessary, while heating gently; after cooling the solution is made up to the required volume and sterile-filtered through a suitable 0.22 μm membrane filter.

B. Water-miscible solvent (medium rate of release)

| an active ingredient from the Tables | 0.1–1.0 g |
|---|---|
| 4-hydroxymethyl-1,3-dioxolan (glycerol formal) | 40 g |
| 1,2-propanediol | ad 100 ml |
| an active ingredient from the Tables | 0.1–1.0 g |
| glycerol dimethyl ketal | 40 g |
| 1,2-propanediol | 100 ml |

Preparation: The active ingredient is dissolved in a portion of the solvent while stirring and the solution is made up to the required volume and sterile-filtered through a suitable 0.22 μm membrane filter.

C. Aqueous solubilisate (rapid release)

| an active ingredient from the Tables | 0.1–1.0 g |
|---|---|
| polyethoxylated castor oil (40 ethylene oxide units)* | 10 g |
| 1,2-propanediol | 20 g |
| benzyl alcohol | 1 g |
| aqua ad. inject. | ad 100 ml |
| an active ingredient from the Tables | 0.1–1.0 g |
| polyethoxylated sorbitan monooleate (20 ethylene oxide units)** | 8 g |
| 4-hydroxymethyl-1,3-dioxolan (glycerol formal) | 20 g |
| benzyl alcohol | 1 g |
| aqua ad. inject. | ad 100 ml |

*Commercially available under the name CREMOPHOR ® EL (BASF AG);
**Commercially available under the name TWEEN ® 80 (ICI);

Preparation: The active ingredient is dissolved in the solvents and the surfactant and made up to the required volume with water. Sterile-filtration through a suitable membrane filter of 0.22 μm pore diameter.

The aqueous systems can be used advantageously also for oral and/or intraruminal administration.

If the active ingredients of formula I or compositions containing them are used for controlling endoparasitic nematodes, cestodes and trematodes in domestic animals and productive livestock, for example cattle, sheep, goats, cats and dogs, they can be administered to the animals in both single and repeated doses, and depending upon the species of animal, the individual doses are preferably from 0.1 to 10 mg/kg of body weight. A better action is often achieved by protracted administration, or lower total doses may also suffice. The active ingredient, or compositions containing it, can also be added to feeds or drinks. The ready-prepared feed contains the active ingredient combinations preferably in a concentration of from 0.005 to 0.1% by weight. The compositions can be administered to the animals perorally in the form of solutions, emulsions, suspensions, powders, tablets, boli or capsules. If the physical and toxicological properties of solutions or emulsions permit it, the compounds of formula I, or compositions containing them, can also be administered to the animals, for example, by subcutaneous injection or intraruminally, or can be applied to the bodies of the animals by the pour-on method. Administration of the active ingredient to animals by means of salt licks or molasses blocks is also possible.

BIOLOGICAL EXAMPLES

B-1. Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm of active ingredient is obtained. About 30 *Lucilia sericata* larvae ($L_1$) are put into each test tube sample. A mortality count is made after 4 days. The compounds of formula I, such as, for example, Nos. 3.2, 3.6, 3.7, 3.10, 3.34 and 3.38, achieved 100% action at 125 ppm.

B-2. Aaricidal action against *Boophilus microplus* (Biarra strain)

Adhesive tape is so applied horizontally across a PVC plate that 10 female *Boophilus microplus* ticks (Biarra strain), fully replete with blood, can be affixed thereto, by their backs, side by side in a row. Each tick is injected from an injection needle with 1 μl of a liquid which represents a 1:1 mixture of polyethylene glycol and acetone, in which mixture a specific amount of active ingredient of 1.0 μg per tick is dissolved. Control ticks are injected with liquid that does not contain the active ingredient. After this treatment, the ticks are kept in an insectarium under normal conditions at about 28° C. and 80% relative humidity until oviposition has taken place and the larvae have hatched from the eggs of the control ticks.

Compounds of formula I, such as, for example, those of the Preparation Examples, at this concentration have the effect that even after 30 days 9 out of 10 female ticks (=90%) lay eggs from which larvae are unable to hatch.

B-3. Trial with sheep infected with nematodes (*Haemonchus contortus* and *Trichostrongylus colubriformis*)

The test compound is administered in the form of a suspension with a stomach probe or by intraruminal injection to sheep which have been artificially infected with *Haemonchus contortus* and *Trichostrongylus colubriformis*. 1 to 3 animals are used for each dose. Each sheep is treated only once with a single dose of 1 mg or 0.2 mg/kg of body weight. Evaluation is made by comparing the number of worm eggs excreted in the faeces of the sheep before and after treatment. Sheep injected simultaneously and in the same manner but untreated are used as controls. In this test, compounds of formula I, such as, for example, those of the Preparation Examples, exhibit a good action at a dose of 0.2 mg/kg, that is to say in comparison with untreated and infected control groups, the treated sheep exhibit no nematode infestation (=complete reduction of the number of worm eggs in the faeces).

B-4. Larvicidal action against *Aedes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, about 30 to 40 three day-old Aedes larvae are put into each beaker. Mortality counts are made after 1, 2 and 5 days.

In this test, compounds of formula I, such as, for example, those of the Preparation Examples, achieved complete kill of all larvae after 1 day at a concentration of 1.6 ppm.

B-5. Milbicidal action against *Dermanyssus gallinae*

2 to 3 ml of a test solution (100, 10, 1 and 0.1 ppm of test compound) are put into a glass container which is open at the top, and about 200 mites in different stages of development are put into the container. The glass container is then sealed with cotton wool and shaken uniformly for 10 minutes until the mites are completely wetted. The container is then inverted until excess test solution has been absorbed by the cotton wool. The container is again inverted and the treated mites are kept under observation for 3 days under laboratory conditions to evaluate the effectiveness of the test compounds, mortality being the criterion for effectiveness.

Compounds of formula I, such as, for example, those of the Preparation Examples, are 100% effective at 100 ppm.

I claim:

1. A compound of formula I

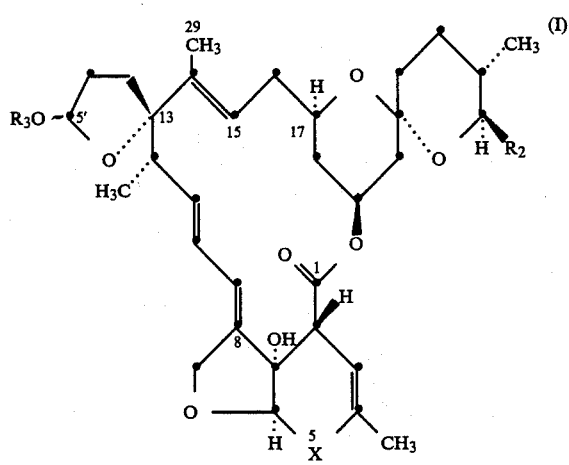

in which

X represents one of the groups —CH(OR$_1$)—, —C(=O)— or —C(=N—OH)—;

R$_1$ represents hydrogen or a OH-protecting group;

R$_2$ represents methyl, ethyl, isopropyl or sec.-butyl or the group —C(CH$_3$)=CH—A in which A represents methyl, ethyl or isopropyl; and R$_3$ represents hydrogen; C$_1$-C$_{10}$-alkyl; C$_1$-C$_{10}$-alkyl substituted by at least one substituent selected from the group consisting of halogen, C$_1$-C$_6$-alkoxy, C$_2$-C$_6$-alkoxyalkoxy, C$_3$-C$_9$-alkoxyalkoxyalkoxy, C$_1$-C$_6$-alkylthio, C$_3$-C$_7$-cycloalkyl, C$_1$-C$_3$-alkyl-substituted C$_3$-C$_7$-cycloalkyl, hydroxy, benzyloxy, C$_1$-C$_6$-acyl and C$_1$-C$_6$-acyloxy, it being possible for each of the above-mentioned radicals representing or containing an alkoxy group to be terminally substituted at a terminal alkoxy group by hydroxy, halogen, C$_1$-C$_6$-acyl or by C$_1$-C$_6$-acyloxy; C$_3$-C$_7$-cycloalkyl; C$_3$-C$_7$-cycloalkyl substituted by at least one substituent selected from the group consisting of halogen and C$_1$-C$_3$-alkyl; C$_3$-C$_7$-cycloalkenyl; C$_2$-C$_{10}$-alkenyl; C$_2$-C$_{10}$-alkynyl; a radical selected from the group consisting of C$_2$-C$_{10}$-alkenyl and C$_2$-C$_{10}$-alkynyl, which radical is substituted by halogen, C$_1$-C$_6$-alkoxy or by C$_1$-C$_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, C$_1$-C$_3$-alkyl, C$_1$-C$_3$-haloalkyl, C$_1$-C$_3$-alkoxy, C$_1$-C$_3$-haloalkoxy, C$_1$-C$_3$-alkythio, nitro and cyano; benzyl substituted by a phenoxy group; or a four- to six-membered heterocyclic radical that has from one to three hetero atoms selected from the group consisting of oxygen, sulphur and nitrogen and that is unsubstituted or is substituted by at least one substituent selected from the group consisting of halogen, C$_1$-C$_3$-alkyl, C$_1$-C$_3$-haloalkyl, C$_1$-C$_3$-alkoxy, C$_1$-C$_3$-haloalkoxy, C$_1$-C$_3$-alkylthio, nitro and cyano, it being possible for the said heterocyclic radical also to be bonded via a C$_1$-C$_6$-alkylene bridge to the oxygen atom in the 5'-position of the tetrahydrofuran ring.

2. A compound of formula I according to claim 1, in which

X represents one of the groups —CH(OR$_1$)— and —C(=N—OH)—,

R$_1$ represents hydrogen or a OH-protecting group;

R$_2$ represents methyl, ethyl, isopropyl or sec.-butyl; and

R$_3$ represents hydrogen; C$_1$-C$_{10}$-alkyl; C$_1$-C$_{10}$-alkyl substituted by at least one substituent selected from the group consisting of halogen, C$_1$-C$_6$-alkoxy, C$_2$-C$_6$-alkoxyalkoxy, C$_3$-C$_9$-alkoxyalkoxyalkoxy, C$_1$-C$_6$-alkylthio, C$_3$-C$_7$-cycloalkyl, hydroxy and C$_1$-C$_6$-acyl, it being possible for each of the above-mentioned radicals representing or containing an alkoxy group to be terminally substituted at a terminal alkoxy group by hydroxy, halogen, C$_1$-C$_6$-acyl or by C$_1$-C$_6$-acyloxy; an ethyl group substituted by benzyloxy; C$_3$-C$_7$-cycloalkyl; C$_3$-C$_7$-cycloalkyl substituted by at least one substituent selected from the group consisting of halogen and C$_1$-C$_3$-alkyl; C$_3$-C$_7$-cycloalkenyl; C$_2$-C$_{10}$-alkenyl; C$_2$-C$_{10}$-alkynyl; a radical selected from the group consisting of C$_2$-C$_{10}$-alkenyl and C$_2$-C$_{10}$-alkynyl, which radical is substituted by halogen, C$_1$-C$_6$-alkoxy or by C$_1$-C$_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, C$_1$-C$_3$-alkyl, C$_1$-C$_3$-haloalkyl, C$_1$-C$_3$-alkoxy, C$_1$-C$_3$-haloalkoxy, C$_1$-C$_3$-alkylthio, nitro and cyano; benzyl substituted by a phenoxy group; or a four- to six-membered heretocyclic radical that has from one to three hetero atoms selected from the group consisting of oxygen, sulphur and nitrogen and that is unsubstituted or is substituted by at least one substituent selected from the group consisting of halogen, C$_1$-C$_3$-alkyl, C$_1$-C$_3$-haloalkyl, C$_1$-C$_3$-alkoxy, C$_1$-C$_3$-haloalkoxy, C$_1$-C$_3$-alkylthio, nitro and cyano, it being possible for the said heterocyclic radical also to be bonded via a C$_1$-C$_6$-alkylene bridge to the oxygen atom in the 5'-position of the tetrahydrofuran ring.

3. A compound of formula I according to claim 2, in which X represents —CH(OR$_1$)—; R$_1$ represents hydrogen or a OH-protecting group; and R$_2$ and R$_3$ have the meaning given in claim 2.

4. A compound of formula I according to claim 1, in which

X represents —CH(OR$_1$)—;

R$_1$ represents hydrogen or a OH-protecting group;

R$_2$ represents methyl, ethyl, isopropyl or sec.-butyl; and

R$_3$ represents hydrogen; C$_1$-C$_{10}$-alkyl; C$_1$-C$_{10}$-alkyl substituted by at least one substituent selected from the group consisting of halogen, C$_1$-C$_6$-alkoxy, C$_2$-C$_6$-alkoxyalkoxy, C$_3$-C$_9$-alkoxyalkoxyalkoxy, C$_1$-C$_6$-alkylthio, C$_3$-C$_7$-cycloalkyl, hydroxy and C$_1$-C$_6$-acyl, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$-alkoxy or by $C_1$–$C_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano; or a four- to six-membered heterocyclic radical that has from one to three hetero atoms selected from the group consisting of oxygen, sulphur and nitrogen and that is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano, it being possible for the said heterocyclic radical also to be bonded via a $C_1$–$C_6$-alkylene bridge to the oxygen atom in the 5'-position of the terahydrofuran ring.

5. A compound of formula I according to claim 4, in which X represents —CH(OR$_1$)— and R$_1$ represents hydrogen, R$_4$—C(O)— or —Si(R$_5$)(R$_6$)(R$_7$); wherein R$_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R$_5$, R$_6$ and R$_7$, independently of one another, represent $C_1$–$C_6$-alkyl, benzyl or phenyl; R$_2$ represents methyl, ethyl, isopropyl or sec.-butyl; and R$_3$ represents hydrogen, $C_1$–$C_5$-alkyl; $C_1$–$C_5$-alkyl substituted by at least one substituent selected from the group consisting of halogen, $C_1$–$C_3$-alkoxy, $C_2$–$C_6$-alkoxyalkoxy, $C_3$–$C_9$-alkoxyalkoxyalkoxy, $C_1$–$C_3$-alkylthio, $C_3$–$C_7$-cycloalkyl, hydroxy and $C_1$–$C_6$-acyl, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of fluorine, chlorine, bromine and methyl; $C_2$–$C_6$-alkenyl; $C_2$–$C_6$-alkynyl; a radical selected from the group consisting of $C_2$–$C_6$-alkenyl and $C_2$–$C_6$-alkynyl, which radical is substituted by fluorine, chlorine, bromine, $C_1$–$C_3$-alkoxy or by $C_1$–$C_6$-acyloxy; phenyl; ben zyl; α-naphthyl; β-naphthyl; a radical selected from the group consisting of phenyl, benzyl, α-naphthyl and β-naphthyl, which radical is substituted by at least one substituent selected from the group consisting of fluorine, chlorine, bromine, methyl, methoxy, CF$_3$, CF$_3$O, CH$_3$S, nitro and cyano; or a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, CF$_3$, CH$_3$O, CF$_3$O, CH$_3$S, nitro and cyano, it being possible for the said heterocyclic radical also to be bonded via a $C_1$–$C_6$-alkylene bridge to the oxygen atom in the 5'-position of the tetrahydrofuran ring.

6. A compound of formula I according to claim 5, in which X represents —CH(OR$_1$)— and R$_1$ represents hydrogen, R$_4$—C(O)— or —Si(R$_5$)(R$_6$)(R$_7$); wherein R$_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R$_5$, R$_6$ and R$_7$, independently of one another, represent $C_1$–$C_4$-alkyl, benzyl or phenyl; R$_2$ represents methyl, ethyl, isopropyl or sec.-butyl; and R$_3$ represents $C_1$–$C_5$-alkyl, or $C_1$–$C_5$-alkyl substituted by at least one substituent selected from the group consisting of halogen, $C_1$–$C_3$-alkoxy, $C_2$–$C_6$-alkoxyalkoxy, $C_3$–$C_9$-alkoxyalkoxyalkoxy, $C_1$–$C_3$-alkylthio, $C_3$–$C_7$-cycloalkyl, hydroxy and $C_1$–$C_6$-acyl, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy.

7. A compound of formula I according to claim 5, in which X represents —CH(OR$_1$)— and R$_1$ represents hydrogen, R$_4$—C(O)— or —Si(R$_5$)(R$_6$)(R$_7$); wherein R$_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R$_5$, R$_6$ and R$_7$, independently of one another, represent $C_1$–$C_4$-alkyl, benzyl or phenyl; R$_2$ represents methyl, ethyl, isopropyl or sec.-butyl; and R$_3$ represents $C_3$–$C_7$-cycloalkyl; $C_3$–$C_7$-cycloalkyl substituted by at least one substituent selected from the group consisting of fluorine, chlorine, bromine and methyl; $C_2$–$C_6$-alkenyl; $C_2$–$C_6$-alkynyl; a radical selected from the group consisting of $C_2$–$C_6$-alkenyl and $C_2$–$C_6$-alkynyl, which radical is substituted by fluorine, chlorine, bromine, $C_1$–$C_3$-alkoxy or by $C_1$–$C_6$-acyloxy; phenyl; benzyl; α-naphthyl; β-naphthyl; a radical selected from the group consisting of phenyl, benzyl, α-naphthyl and β-naphthyl, which radical is substituted by at least one substituent selected from the group consisting of fluorine, chlorine, bromine, methyl, methoxy, CF$_3$, CF$_3$O, CH$_3$S, nitro and cyano; or a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, CF$_3$, CH$_3$O, CF$_3$O, CH$_3$S, nitro and cyano, it being possible for the said heterocyclic radical also to be bonded via a $C_1$–$C_6$-alkylene bridge to the oxygen atom in the 5'-position of the terahydrofuran ring.

8. A compound of formula I according to claim 5, in which X represents —CH(OR$_1$)— and R$_1$ represents hydrogen, R$_4$—C(O)— or —Si(R$_5$)(R$_6$ )(R$_7$); wherein R$_4$ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R$_5$, R$_6$ and R$_7$, independently of one another, represent $C_1$–$C_4$-alkyl, benzyl or phenyl; R$_2$ represents methyl, ethyl, isopropyl or sec.-butyl; and R₃ represents phenyl, benzyl, α-naphthyl, β-naphthyl or a radical selected from the group consisting of phenyl, benzyl, α-naphthyl and β-naphthyl, which radical is substituted by at least one substituent selected from the group consisting of fluorine, chlorine, bromine, methyl, methoxy, $CF_3$, $CF_3O$, $CH_3S$, nitro and cyano.

9. A compound of formula I according to claim 5, in which X represents —CH(OR₁)— and R₁ represents hydrogen, R₄—C(O)— or —Si(R₅)(R₆)(R₇); wherein R₄ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R₅, R₆ and R₇, independently of one another, represent $C_1$–$C_4$-alkyl, benzyl or phenyl; R₂ represents methyl, ethyl, isopropyl or sec.-butyl; and R₃ represents a four- to six-membered heterocyclic radical that has from one to three hetero atoms selected from the group consisting of oxygen, sulphur and nitrogen and that is unsubstituted or is substituted by at least one substituent selected from the group consisting of fluorine, chlorine, bromine, methyl, ethyl, $CF_3$, $CH_3O$, $CF_3O$, $CH_3S$, nitro and cyano, it being possible for the said heterocyclic radical also to be bonded via a $C_1$–$C_6$-alkylene bridge to the oxygen atom in the 5'-position of the tetrahydrofuran ring.

10. A compound of formula I according to claim 9, in which X represents —CH(OR₁)— and R₁ represents hydrogen, R₄—C(O)— or —Si(R₅)(R₆)(R₇); wherein R₄ represents $C_1$–$C_{10}$-alkyl, $C_1$–$C_{10}$-haloalkyl or a radical selected from the group consisting of phenyl and benzyl, which radical is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, cyano and nitro, and R₅, R₆ and R₇, independently of one another, represent $C_1$–$C_4$-alkyl, benzyl or phenyl; R₂ represents methyl, ethyl, isopropyl or sec.-butyl; and R₃ represents an unsaturated or preferably saturated four-membered heterocyclic radical having a hetero atom selected from the group consisting of oxygen, nitrogen and sulphur, or represents furan, thiophene, pyrrole, isoxazole, isothiazole, furazan, imidazole, 1,2,4-triazole, 1,2,3-triazole, pyrazole, pyrroline, oxazole, thiazole, thiadiazoles, pyrazoline, thiazoline, pyrazolidine, pyrrolidine, oxazolidine, thiazolidine, oxadiazole, imidazoline, imidazolidine, pyrazolidine, tetrahydrofuran, pyridine, pyridazine, pyrimidine, pyrazine, thiazine, thiadiazines, pyrans, piperidine, piperazine, morpholine, perhydrothiazine or dioxan, it being possible for the said heterocyclic radical also to be bonded via a $C_1$–$C_4$-alkylene bridge to the oxygen atom in the 5'-position of the tetrahydrofuran ring.

11. A compound of formula I according to claim 1, in which X represents —CH(OR₁)— and R₁ represents hydrogen; R₂ represents ethyl; and R₃ represents $C_4$–$C_5$-alkyl, $C_4$–$C_6$-cycloalkyl, $C_4$–$C_6$-cycloalkyl bonded via methyl, or phenyl, benzyl or α-methylbenzyl.

12. A compound of formula I according to claim 1 in which R₂ represents methyl or ethyl and X and R₃ have the meanings given in claim 1.

13. A compound of formula I according to claim 12, in which R₂ represents ethyl.

14. A compound of formula I according to claim 4, selected from the group:
milbemycin A₄-13-spiro-2'-[5'-(2''-ethoxyethoxy)-tetrahydrofuran],
milbemycin A₄-13-spiro-2'-[5'-(2'',2''-dimethylpropoxy)-tetrahydrofuran],
milbemycin A₄-13-spiro-2'-[5'-cyclohexyloxytetrahydrofuran],
milbemycin A₄-13-spiro-2'-[5'-benzyloxytetrahydrofuran],
milbemycin A₄-13-spiro-2'-[5'-{2''-(2'''-(methoxyethoxy)-ethoxy}-tetrahydrofuran],
milbemycin A₄-13-spiro-2'-[5'-{2''-(2'''-(hydroxymethoxy)-ethoxy)-ethoxy}-tetrahydrofuran],
milbemycin A₄-13-spiro-2'-[5'-{2''-(2'''-(chloroacetoxy)-ethoxy)-ethoxy}-tetrahydrofuran],
milbemycin A₄-13-spiro-2'-[5'-methoxytetrahydrofuran], and
milbemycin A₄-13-spiro-2'-[5'-(2''-hydroxyethoxy)-tetrahydrofuran].

15. A compound of formula I according to claim 11, selected from the group:
milbemycin A₄-13-spiro-2'-[5'-(2''-methylbutoxy)-tetrahydrofuran] and
milbemycin A₄-13-spiro-2 '-[5'-(1''-methylpropoxy)-tetrahydrofuran].

16. A composition for controlling ecto- and endoparasites in productive livestock or for controlling pest insects, characterised in that, in addition to customary carriers and dispersing agents, it contains a compound of formula I

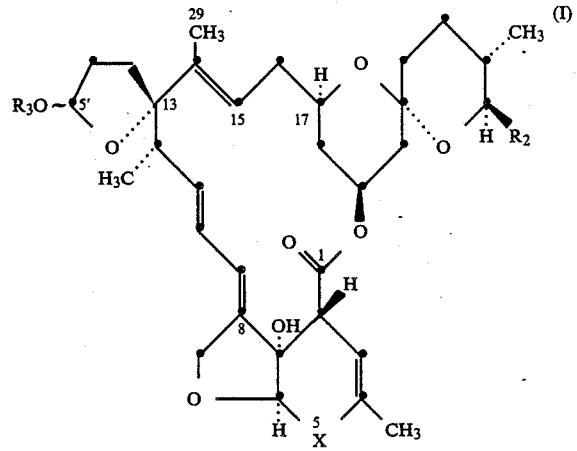

in which
X represents one of the groups —CH(OR₁)—, —C(=O)— or —C(=N—OH)—;
R₁ represents hydrogen or a OH-protecting group;
R₂ represents methyl, ethyl, isopropyl or sec.-butyl or the group —C(CH₃)=CH—A in which A represents methyl, ethyl or isopropyl; and
R₃ represents hydrogen; $C_1$–$C_{10}$-alkyl; $C_1$–$C_{10}$-alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, $C_1$–$C_3$-alkyl-substituted $C_3$–$C_7$-cycloalkyl, hydroxy, benzyloxy, $C_1$–$C_6$-acyl and $C_1$–$C_6$-acyloxy, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$-alkoxy or by $C_1$–$C_6$-acyloxy; 1-adamantylmethyl; methyl; carveyl; phenyl; benzyl; naphthyl; a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano; benzyl substituted by a phenoxy group; or a four- to six-membered heterocyclic radical that has from one to three hetero atoms selected from the group consisting of oxygen, sulphur and nitrogen and that is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano, it being possible for the said heterocyclic radical also to be bonded via a $C_1$–$C_6$-alkylene bridge to the oxygen atom in the 5'-position of the tetrahydrofuran ring.

17. A composition according to claim 16, characterised in that it contains as active ingredient a compound of formula I, in which X represents —CH(OR$_1$)— and R$_1$ represents hydrogen; R$_2$ represents ethyl; and R$_3$ represents $C_4$–$C_5$-alkyl, $C_4$–$C_6$-cycloalkyl, $C_4$–$C_6$-cycloalkyl bonded via methyl, or phenyl, benzyl or a α-methylbenzyl.

18. A method of controlling parasites in animals or of controlling insect pests, characterised in that a parasiticidally or insecticidally effective amount of a compound of formula I

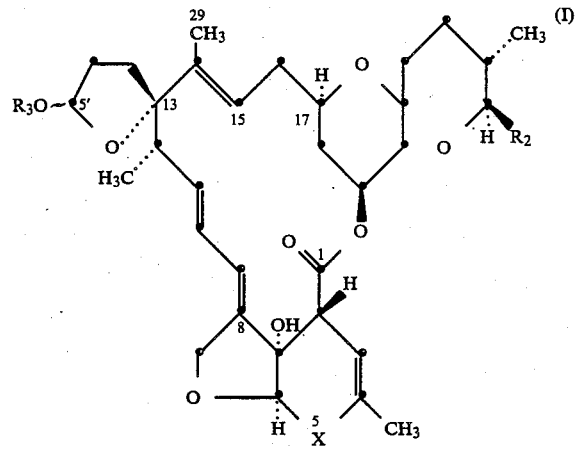

in which
X represents one of the groups —CH(OR$_1$)—, —C(=O)— or —C(=N—OH)—;
R$_1$ represents hydrogen or a OH-protecting group;
R$_2$ represents methyl, ethyl, isopropyl or sec.-butyl or the group —C(CH$_3$)=CH—A in which A represents methyl, ethyl or isopropyl; and
R$_3$ represents hydrogen; $C_1$–$C_{10}$-alkyl; $C_1$–$C_{10}$-alkyl substituted by at least one substituent selected from the group consisting of halogen, $C_1$–$C_6$-alkoxy, $C_2$–$C_6$-alkoxyalkoxy, $C_3$–$C_9$-alkoxyalkoxyalkoxy, $C_1$–$C_6$-alkylthio, $C_3$–$C_7$-cycloalkyl, $C_1$–$C_3$-alkyl-substituted $C_3$–$C_7$-cycloalkyl, hydroxy, benzyloxy, $C_1$–$C_6$-acyl and $C_1$–$C_6$-acyloxy, it being possible for each of the above-mentioned radicals representing or containing an alkoxy group to be terminally substituted at a terminal alkoxy group by hydroxy, halogen, $C_1$–$C_6$-acyl or by $C_1$–$C_6$-acyloxy; $C_3$–$C_7$-cycloalkyl; $C_3$–$C_7$-cycloalkyl substituted by at least one substituent selected from the group consisting of halogen and $C_1$–$C_3$-alkyl; $C_3$–$C_7$-cycloalkenyl; $C_2$–$C_{10}$-alkenyl; $C_2$–$C_{10}$-alkynyl; a radical selected from the group consisting of $C_2$–$C_{10}$-alkenyl and $C_2$–$C_{10}$-alkynyl, which radical is substituted by halogen, $C_1$–$C_6$-alkoxy or by $C_1$–$C_6$-acyloxy; 1-adamantylmethyl; menthyl; carveyl; phenyl; benzyl; naphthyl; a radical selected from the group consisting of phenyl, benzyl and naphthyl, which radical is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano; benzyl substituted by a phenoxy group; or a four- to six-membered heterocyclic radical that has from one to three hetero atoms selected from the group consisting of oxygen, sulphur and nitrogen and that is unsubstituted or is substituted by at least one substituent selected from the group consisting of halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, nitro and cyano, it being possible for the said heterocyclic radical also to be bonded via a $C_1$–$C_6$-alkylene bridge to the oxygen atom in the 5'-position of the tetrahydrofuran ring, is applied to the parasite, the insect pest or to the locus thereof.

19. A process according to claim 18, characterised in that the parasites are nematodes.

* * * * *